US008268301B2

(12) United States Patent
Jiang et al.

(10) Patent No.: US 8,268,301 B2
(45) Date of Patent: *Sep. 18, 2012

(54) CATIONIC BETAINE PRECURSORS TO ZWITTERIONIC BETAINES HAVING CONTROLLED BIOLOGICAL PROPERTIES

(75) Inventors: Shaoyi Jiang, Redmond, WA (US); Shengfu Chen, Hangzhou (CN); Zheng Zhang, Cambridge, MA (US); Gang Cheng, Seattle, WA (US); Hong Xue, Seattle, WA (US); Louisa R. Carr, Seattle, WA (US)

(73) Assignee: University of Washington, Seattle, WA (US)

( * ) Notice: Subject to any disclaimer, the term of this patent is extended or adjusted under 35 U.S.C. 154(b) by 772 days.

This patent is subject to a terminal disclaimer.

(21) Appl. No.: 12/274,218

(22) Filed: Nov. 19, 2008

(65) Prior Publication Data

US 2009/0156460 A1  Jun. 18, 2009

Related U.S. Application Data

(60) Provisional application No. 60/989,073, filed on Nov. 19, 2007.

(51) Int. Cl.
*A61K 31/74* (2006.01)
(52) U.S. Cl. ............... 424/78.17; 424/78.18; 424/78.31; 424/78.35
(58) Field of Classification Search .................. None
See application file for complete search history.

(56) References Cited

U.S. PATENT DOCUMENTS

| | | | |
|---|---|---|---|
| 3,671,502 A | 6/1972 | Samour | |
| 4,075,183 A | 2/1978 | Kawakami | |
| 4,138,446 A | 2/1979 | Kawakami | |
| 4,415,388 A | 11/1983 | Korpman | |
| 4,493,926 A | 1/1985 | Williams, Jr. | |
| 4,985,023 A | 1/1991 | Blank | |
| 5,204,060 A | 4/1993 | Allenmark | |
| 5,714,360 A | 2/1998 | Swan | |
| 5,919,523 A | 7/1999 | Sundberg | |
| 6,361,768 B1 | 3/2002 | Galleguillos | |
| 6,486,333 B1 | 11/2002 | Murayama | |
| 6,897,263 B2 | 5/2005 | Hell | |
| 7,291,427 B2 | 11/2007 | Kawamura | |
| 7,306,625 B1 | 12/2007 | Stratford | |
| 7,335,248 B2 | 2/2008 | Abou-Nemeh | |
| 7,737,224 B2 | 6/2010 | Willis | |
| 2005/0058689 A1 | 3/2005 | McDaniel | |
| 2006/0240072 A1 | 10/2006 | Chudzik | |
| 2007/0042198 A1 | 2/2007 | Schonemyr | |

FOREIGN PATENT DOCUMENTS

| | | |
|---|---|---|
| EP | 0 354 984 A2 | 2/1990 |
| EP | 0 419 654 A1 | 4/1991 |
| EP | 0 479 245 A2 | 4/1992 |
| JP | 63-234007 A | 9/1988 |
| RU | 1780673 A1 | 12/1992 |
| SU | 1780673 A1 | 12/1992 |
| WO | 00/39176 A1 | 7/2000 |
| WO | 2004/058837 A2 | 7/2004 |
| WO | 2004/100666 A1 | 11/2004 |
| WO | 2007/068744 A1 | 6/2007 |
| WO | 2007/099239 A2 | 9/2007 |

OTHER PUBLICATIONS

International Search Report and Written Opinion mailed Jan. 29, 2009, issued in corresponding International Application No. PCT/US2008/084095, filed Nov. 19, 2008.
Chang, Y., et al., "Highly Protein-Resistant Coatings From Well-Defined Diblock Copolymers Containing Sulfobetaines," Langmuir 22(5):2222-2226, Feb. 2006.
Chen, S., et al., "Controlling Antibody Orientation on Charged Self-Assembled Monolayers," Langmuir 19(7):2859-2864, Apr. 2003.
Chen, S., et al., "Strong Resistance of Oligo(phosphorylcholine) Self-Assembled Monolayers to Protein Adsorption," Langmuir 22(6):2418-2421, Mar. 2006.
Chen, S., et al., "Strong Resistance of Phosphorylcholine Self-Assembled Monolayers to Protein Adsorption: Insights Into Nonfouling Properties of Zwitterionic Materials," Journal of the American Chemical Society 127(41):14473-14478, Oct. 2005.
Feng, W., et al., "Adsorption of Fibrinogen and Lysozyme on Silicon Grafted With Poly(2-methacryloyloxyethyl phosphorylcholine) Via Surface-Initiated Atom Transfer Radical Polymerization," Langmuir 21(13):5980-5987, Jun. 2005.
Feng, W., et al., "Atom-Transfer Radical Grafting Polymerization of 2-Methacryloyloxyethyl Phosphorylcholine From Silicon Wafer Surfaces,"Journal of Polymer Science: Part A: Polymer Chemistry 42(12)2931-2942, Jun. 2004.
Jiang, Y., et al., "Blood Compatibility of Polyurethane Surface Grafted Copolymerization With Sulfobetaine Monomer," Colloids and Surfaces B: Biointerfaces 36(1):27-33, Jul. 2004.
Jun, Z., et al., "Surface Modification of Segmented Poly(ether urethane) by Grafting Sulfo Ammonium Zwitterionic Monomer to Improve Hemocompatibilities," Colloids and Surfaces B: Biointerfaces 28(1):1-9, Apr. 2003.
Li, L., et al., "Protein Adsorption on Alkanethiolate Self-Assembled Monolayers: Nanoscale Surface Structural and Chemical Effects," Langmuir 19(7):2974-2982, Apr. 2003.
Li, L. et al., "Protein Adsorption on Oligo(ethylene glycol)-Terminated Alkanethiolate Self-Assembled Monolayers: The Molecular Basis for Nonfouling Behavior," Journal of Physical Chemistry B 109(7):2934-2941, Feb. 2005.
Lowe, A.B., et al., "Well-Defined Sulfobetaine-Based Statistical Copolymers as Potential Antibioadherent Coatings," Journal of Biomedical Materials Research 52(1):88-94, Jul. 2000.
West, S.L., et al., "The Biocompatibility of Crosslinkable Copolymer Coatings Containing Sulfobetaines and Phosphobetaines," Biomaterials 25:1195-1204, Apr. 2004.

(Continued)

*Primary Examiner* — James Rogers
(74) *Attorney, Agent, or Firm* — Christensen O'Connor Johnson Kindness PLLC

(57) ABSTRACT

Cationic polymers hydrolyzable to zwitterionic polymers, monomers for making the cationic polymers, surfaces that include the polymers, therapeutic agent delivery systems that include the cationic polymers, methods for administering a therapeutic agent using the delivery systems, and methods for making and using the cationic polymers, monomers, surfaces, and therapeutic agent delivery systems.

20 Claims, 22 Drawing Sheets

OTHER PUBLICATIONS

Yuan, J., et al., "Chemical Graft Polymerization of Sulfobetaine Monomer on Polyurethane Surface for Reduction in Platelet Adhesion," Colloids and Surfaces B: Biointerfaces 39(1-2):87-94, Nov. 2004.

Yuan, J., et al., "Improvement of Blood Compatibility on Cellulose Membrane Surface by Grafting Betaines," Colloids and Surfaces B: Biointerfaces 30(1-2):147-155, Jul. 2003.

Yuan, J., "Platelet Adhesion Onto Segmented Polyurethane Surfaces Modified by Carboxybetaine," Journal of Biomaterial Science, Polymer Edition 14(12):1339-1349, Dec. 2003.

Yuan, Y., et al., "Grafting Sulfobetaine Monomer Onto Silicone Surface to Improve Haemocompatability," Polymer International 53(1):121-126, Jan. 2004.

Yuan, Y., et al. "Grafting Sulfobetaine Monomer Onto the Segmented Poly(ether-urethane) Surface to Improve Hemocompatability," Journal of Biomaterials Science, Polymer Edition 13(10):1081-1092, Oct. 2002.

Yuan, Y., et al., "Polyurethane Vascular Catheter Surface Grafted With Zwitterionic Sulfobetaine Monomer Activated by Ozone," Colloids and Surfaces B: Biointerfaces 35(1):1-5, May 2004.

Yuan, Y., et al., "Surface Modification of SPEU Films by Ozone Induced Graft Copolymerization to Improve Hemocompatibility," Colloids and Surfaces B: Biointerfaces 29(4):247-256, Jun. 2003.

Zhang, J., et al., "Chemical Modification of Cellulose Membranes With Sulfo Ammonium Zwitterionic Vinyl Monomer to Improve Hemocompatibility," Colloids and Surfaces B: Biointerfaces 30(3):249-257, Jul. 2003.

Zhang, Z., et al., "The Hydrolysis of Cationic Polycarboxybetaine Esters to Zwitterionic Polycarboxybetaines With Controlled Properties," Biomaterials 29(36):4719-4725, Dec. 2008.

Zhang, Z., et al., "Superflow Fouling Sulfobetaine and Carboxybetaine Polymers on Glass Slides," Langmuir 22(24):10072-10077, Nov. 2006.

Zhang, Z., "Surface Grafted Sulfobetaine Polymers Via Atom Transfer Radical Polymerization as Superlow Fouling Coatings," Journal of Physical Chemistry B 110(22):10799-10804, Jun. 2006.

Zheng, J., "Molecular Simulation Study of Water Interactions With Oligo (Ethylene Glycol)-Terminated Alkanethiol Self-Assembled Monolayers," Langmuir 20(20):8931-8938, Sep. 2004.

Zheng, J., "Strong Repulsive Forces Between Protein and Oligo (Ethylene Glycol) Self-Assembled Monolayers: A Molecular Simulation Study," Biophysical Journal 89(1):158-166, Jul. 2005.

Zhou, J., et al., "Platelet Adhesion and Protein Adsorption on Silicone Rubber Surface by Ozone-Induced Grafted Polymerization With Carboxybetaine Monomer," Colloids and Surfaces B: Biointerfaces 41(1):55-62, Mar. 2005.

Communication Pursuant to Article 94(3) EPC, mailed Oct. 19, 2010, issued in corresponding European Application No. 08851463.3, filed Nov. 19, 2008, 4 pages.

"Betaine," Wikipedia, The Free Encyclopedia, <http://en.wikipedia.org/wiki/Betaine> [retrieved Jul. 31, 2011], 1 page.

"Bromide," Wikipedia, The Free Encyclopedia, <http://en.wikipedia.org/wiki/Bromide> [retrieved Jul. 27, 2011] 3 pages.

"Nail Infections," Health911, <http://www.health911.com/nail-infections> [retrieved Aug. 29, 2011], 3 pages.

CBAA-1-ester

CBAA-3-ester

CBAA-5-ester

CBMA-1 C2 SA

CATIONIC BETAINE PRECURSORS TO ZWITTERIONIC BETAINES HAVING CONTROLLED BIOLOGICAL PROPERTIES

CROSS-REFERENCE TO RELATED APPLICATION

This application claims the benefit of U.S. Provisional Application No. 60/989,073, filed Nov. 19, 2007, expressly incorporated herein by reference in its entirety.

STATEMENT OF GOVERNMENT LICENSE RIGHTS

This invention was made with Government support under Grant No. N000140410409 awarded by the Office of Naval Research and Grant No. AB06BAS759 awarded by the Defense Threat Reduction Agency, U.S. Department of Defense. The Government has certain rights in the invention.

BACKGROUND OF THE INVENTION

Cationic polymers have many unique biological, chemical, and mechanical properties. It is well known that cationic polymers can condense DNA or proteins or proteins for gene or drug delivery. Polycations can be used as an antimicrobial agent to disrupt the membranes of bacteria. However, cationic polymers present cell toxicity and tend to bind proteins that restricts their biomedical applications. For antimicrobial materials, killed microbes can accumulate on the surfaces and decrease their antimicrobial activities.

Despite the usefulness of cationic polymers for biomedical applications, there exists a need for new polymeric materials that offer the advantageous properties of cationic polymers without suffering from their associated disadvantages. The present invention seeks to fulfill this need and provides further related advantages.

SUMMARY OF THE INVENTION

The present invention provides cationic polymers that are hydrolyzable to zwitterionic polymers, cationic monomers that are polymerizable to provide the cationic polymers, surfaces coated with the cationic polymers, methods for applying the cationic polymers to surfaces, therapeutic agent delivery systems that include the cationic polymers, methods for delivering therapeutic agents using the cationic polymers, and methods for making the cationic polymers and the cationic monomers.

In one aspect, the invention a cationic polymer that is hydrolyzable to a zwitterionic polymer. In one embodiment, the cationic polymer comprises:

(a) polymer backbone;

(b) a plurality of cationic centers, each cationic center covalently coupled to the polymer backbone by a first linker;

(c) a counter ion associated with each cationic center; and (d) a hydrolyzable group covalently coupled to each cationic center through a second linker, wherein the hydrolyzable group is hydrolyzable to an anionic center to provide a zwitterionic polymer having the anionic center covalently coupled to the cationic center through the second linker.

In one embodiment, the cationic polymer has the formula:

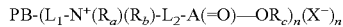

wherein PB is the polymer backbone having n pendant groups $L_1\text{-}N^+(R_a)(R_b)\text{-}L_2\text{-}A(\!=\!O)\text{---}OR_c)$; $N^+$ is the cationic center; $R_a$ and $R_b$ are independently selected from hydrogen, alkyl, and aryl; $A(\!=\!O)\text{---}OR_c$ is the hydrolyzable group, wherein A is selected from the group consisting of C, S, SO, P, or PO, and $R_c$ is an alkyl, aryl, acyl, or silyl group that may be further substituted with one or more substituents; $L_1$ is a linker that covalently couples the cationic center to the polymer backbone; $L_2$ is a linker that covalently couples the cationic center to the hydrolyzable group; $X^-$ is the counter ion associated with the cationic center; and n is an integer from about 10 to about 10,000.

In certain embodiments, the counter ion is a hydrophobic organic counter ion. Representative hydrophobic organic counter ions include C1-C20 carboxylates and C1-C20 alkylsulfonates.

In certain embodiments, the counter ion is a therapeutic agent. Representative therapeutic agents include antimicrobial, antibacterial, and antifungal agents. In one embodiment, the therapeutic agent is a salicylate.

In certain embodiments, the counter ion is selected from nucleic acids (e.g., DNAs, RNAs, and siRNAs), amino acids, proteins, and peptides.

In certain embodiments, the hydrolyzable group releases a hydrophobic organic group on hydrolysis. Representative hydrophobic organic groups include C4-C20 carboxylates (e.g., n-C4-C20 alkyl-$CO_2^-$).

In certain embodiments, the hydrolyzable group releases a therapeutic agent on hydrolysis. Representative therapeutic agents include antimicrobial, antibacterial, and antifungal agents. In one embodiment, the therapeutic agent is a salicylate.

The cationic center is selected from ammonium, imidazolium, triazaolium, pyridinium, morpholinium, oxazolidinium, pyrazinium, pyridazinium, pyrimidinium, piperazinium, and pyrrolidinium cationic centers.

In certain embodiments, $R_a$ and $R_b$ are independently selected from the group consisting of C1-C10 straight chain and branched alkyl groups.

In certain embodiments, $L_1$ is selected from the group consisting of $-C(\!=\!O)O-(CH_2)_n-$ and $-C(\!=\!O)NH-(CH_2)_n-$, wherein n is an integer from 1 to 20.

In certain embodiments, $L_2$ is $-(CH_2)_n-$, where n is an integer from 1 to 20.

In certain embodiments, A is selected from the group consisting of C, SO, and PO.

In certain embodiments, $R_c$ is C4-C20 alkyl.

In certain embodiments, $X^-$ is selected from halides, carboxylates, alkylsulfonates, sulfate; nitrate, perchlorate, tetrafluoroborate, hexafluorophosphate, trifluoromethylsulfonate, bis(trifluoromethylsulfonyl)amide, lactate, and salicylate.

In another aspect, the invention provides monomers for making the cationic polymers of the invention. In one embodiment, the monomer is a cationic compound, comprising:

(a) a polymerizable group;

(b) a cationic center covalently coupled to the polymerizable group by a first linker;

(c) a counter ion associated with the cationic center; and (d) a hydrolyzable group covalently coupled to the cationic center through a second linker, wherein the hydrolyzable group is hydrolyzable to an anionic center to provide a zwitterionic compound having the anionic center covalently coupled to the cationic center through the second linker.

In one embodiment, the compound has the formula

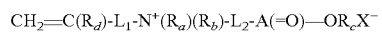

wherein $CH_2\!=\!C(R_d)$ is the polymerizable group, $R_d$ is selected from the group consisting of hydrogen, fluorine, trifluoromethyl, and C1-C6 alkyl; $N^+$ is the cationic center; $R_a$ and $R_b$ are independently selected from hydrogen, alkyl, and aryl; $A(=O)$—$OR_c$ is the hydrolyzable group, wherein A is selected from the group consisting of C, S, SO, P, or PO, and $R_c$ is an alkyl, aryl, acyl, or silyl group that may be further substituted with one or more substituents; $L_1$ is a linker that covalently couples the cationic center to the polymerizable group; $L_2$ is a linker that covalently couples the cationic center to the hydrolyzable group; and $X^-$ is the counter ion associated with the cationic center.

$L_1$, $N^+$, $R_a$, $R_b$, $L_2$, $A(=O)$—$OR_c$, and $X^-$ are as described above for the cationic polymers.

In another aspect, the invention provides polymers obtainable from polymerizing one or more of the monomers described above. In one embodiment, the polymers obtainable from polymerizing one or more of the monomers described above are homopolymers. In another embodiment, the polymers are copolymers. Representative copolymers include random and block copolymers. In one embodiment, the copolymers are obtainable by copolymerizing one or more of the monomers described above with one or more second co-monomers. Representative co-monomers include polymerizable zwitterionic monomers, hydrophobic monomers, and anionic monomers.

In certain embodiments, the polymers obtainable from the cationic monomers of the invention has a plurality of repeating units, with the repeating units having the formula:

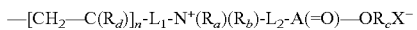

wherein —$[CH_2—C(R_d)]_n$— defines a polymer backbone having n repeating units; $R_d$ is selected from the group consisting of hydrogen, fluorine, trifluoromethyl, and C1-C6 alkyl; n is 10 to 10,000; $N^+$ is a cationic center; $R_a$ and $R_b$ are independently selected from hydrogen, alkyl, and aryl; $A(=O)$—$OR_c$ is a hydrolyzable group, wherein A is selected from the group consisting of C, S, SO, P, or PO, and $R_c$ is an alkyl, aryl, acyl, or silyl group that may be further substituted with one or more substituents; $L_1$ is a linker that covalently couples the cationic center to the polymer backbone; $L_2$ is a linker that covalently couples the cationic center to the hydrolyzable group; and $X^-$ is the counter ion associated with the cationic center.

$L_1$, $N^+$, $R_a$, $R_b$, $L_2$, $A(=O)$—$OR_c$, and $X^-$ are as described above for the cationic polymers.

In one embodiment, the polymer is a homopolymer. In one embodiment, the polymer is a copolymer. In one embodiment, the copolymer is a random copolymer. In another embodiment, the copolymer is a block copolymer. In other embodiments, the copolymer includes a repeating unit selected from hydrophobic repeating units, anionic repeating units, and zwitterionic repeating units.

In another aspect, the invention provides surfaces that are treated with, coated with, modified by, or otherwise incorporates one or more polymers of the invention. In certain embodiments, the invention provides a surface of a substrate that has been treated with, coated with, modified by, or otherwise incorporates one or more polymers of the invention. Representative substrates include particles, drug carriers, non-viral gene delivery systems, biosensors, membranes, implantable sensors, subcutaneous sensors, implants, and contact lenses. Other representative substrates include implantable medical devices such as ear drainage tubes, feeding tubes, glaucoma drainage tubes, hydrocephalous shunts, keratoprostheses, nerve guidance tubes, urinary catheters, tissue adhesives, x-ray guides, artificial joints, artificial heart valves, artificial blood vessels, pacemakers, left ventricular assist devices (LVADs), artery grafts, tissue scaffolds, and stents.

Methods for applying, coating, modifying, or otherwise incorporating one or more polymers of the invention onto a surface of a substrate are also provided. The polymers can be directly applied to a surface by, for example, various deposition techniques including dissolving or suspending in a solvent and then spin coating, painting or spraying. Alternatively, in other embodiments, the surfaces can be substrates onto which the polymers are made by conventional polymerization techniques involving suitable monomers.

In another aspect of the invention, therapeutic agent delivery systems are provided. In one embodiment, the therapeutic agent delivery system includes a polymer of the invention and a therapeutic agent that is reversibly associative with the polymer. Representative therapeutic agents include small molecules, nucleic acids, amino acids, peptides, and proteins. In one embodiment, the therapeutic agent is a nucleic acid such as a DNA, RNA, or siRNA. In certain embodiments, the polymer is a copolymer. Representative copolymers have first repeating units and second repeating units. Suitable first repeating units include tertiary (3°) amine groups and suitable second repeating units include primary (1°), secondary (2°), or quaternary (4°) amine groups. These copolymers can be designated 3°/1°, 3°/2°, and 3°/4°. In one embodiment, the second repeating units include quaternary amine groups (e.g., 3°/4° copolymer). In one embodiment, the copolymers are random copolymers. In another embodiment, the copolymers are block copolymers.

In a further aspect, the invention provides methods for administering a therapeutic agent using a cationic polymer of the invention. In the method, a therapeutic agent is administered to a subject in need thereof by administering a therapeutic agent delivery system that includes a polymer of the invention and a therapeutic agent that is reversibly associative with the polymer.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
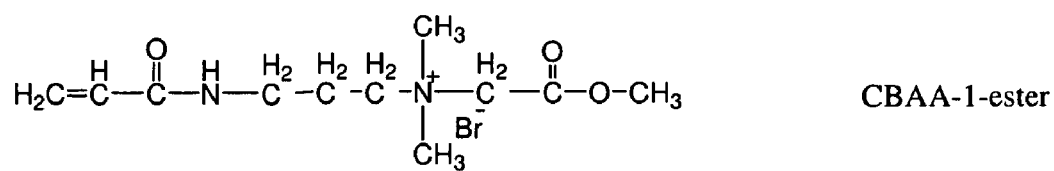
FIG. 1 illustrates the structures of three representative cationic monomers useful for making cationic polymers of the invention: three acrylamide monomers with different carboxybetaine ester groups; CBAA-1-ester, CBAA-3-ester, and CBAA-5-ester.
Figure 1:
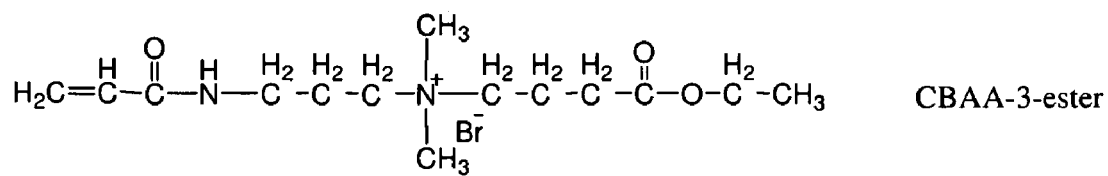
Figure 1:
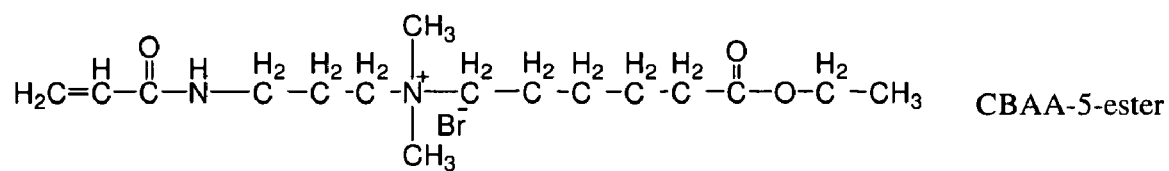

The invention provides polymers, materials made form the polymers, and methods for making and using the polymers and polymer materials.

In one aspect of the invention, cationic polymers are provided. The cationic polymers of the invention include hydrolyzable groups that can be hydrolyzed to provide zwitterionic polymers. Zwitterionic polymers are polymers having a balance of positive and negative charge. Zwitterionic polymers can be highly resistant to protein adsorption and bacterial adhesion. Due to their biomimetic nature, zwitterionic polymers, such as phosphobetaine, sulfobetaine, and carboxybetaine polymers, exhibit high biocompatibility.

Controlled Hydrolysis. The variation of the structural features of the cationic polymers allows for their controlled hydrolysis and the control of the biological, chemical, and mechanical properties. The rate of hydrolysis can be significantly affected by and controlled by the selection of the nature of the hydrolyzable group (e.g., for esters, —OR).

As described below, in certain embodiments, the cationic polymers of the invention advantageously release functional groups on hydrolysis. For example, for cationic esters of the invention, hydrolysis ester releases an —OR group. In these embodiments, the released group can be a therapeutic agent (e.g., an antimicrobial, antibacterial, an antifungal agent). Similarly, in certain embodiments, the cationic polymers can release their counter ions ($X^-$), which can also be therapeutic agents (e.g., nucleic acids, amino acids, peptides, proteins, and salicylate).

For applications as gene or drug delivery carriers, conjugated DNAs or proteins can be released via the hydrolysis of a cationic polymer carrier when the complex reaches its target. For applications as antimicrobial agents, antimicrobial cationic polymers can be converted to zwitterionic polymers, leaving no toxic residues in the environment or no killed microbes on a surface.

It will be appreciated that the hydrolyzable group can be cleaved not only by hydrolysis, but also by cleavage (e.g., degradation or erosion) that occurs by other means. The cationic polymers can be converted to their corresponding zwitterionic polymers by environmental changes due to enzymatic catalysis, redox, heat, light, ionic strength, pH, and hydrolysis, among others. For therapeutic agent delivery applications described below, cleavage likely occurs by enzymatic action and/or pH change.

Representative cationic polymers of the invention and their corresponding zwitterionic polymer counterparts are described below.

Cationic Polymers

The cationic polymers of the invention include hydrolyzable groups that, when hydrolyzed, provide anionic groups that render the polymer zwitterionic. In each polymer, the number of hydrolyzable groups is substantially equal to the number of cationic groups such that, when the hydrolyzable groups are hydrolyzed, in the resulting polymer is zwitterionic. As used herein, the term "zwitterionic polymer" refers to a polymer having substantially equal numbers of cationic groups and anionic groups.

Representative cationic polymers of the invention have formula (I):

$$\text{PB-}(L_1\text{-}N^+(R_a)(R_b)\text{-}L_2\text{-}A(=O)\text{—}OR_c)_n(X^-)_n \quad \text{(I)}$$

wherein PB is the polymer backbone having n pendant groups (i.e., $L_1\text{-}N^+(R_a)(R_b)\text{-}L_2\text{-}A(=O)\text{—}OR_c$); $N^+$ is the cationic center; $R_a$ and $R_b$ are independently selected from hydrogen, alkyl, and aryl groups; $A(=O)\text{—}OR_c$ is the hydrolyzable group, wherein A is C, S, SO, P, or PO, and $R_c$ is an alkyl, aryl, acyl, or silyl group that may be further substituted with one or more substituents; $L_1$ is a linker that covalently couples the cationic center to the polymer backbone; $L_2$ is a linker that covalently couples the cationic center to the hydrolyzable group; $X^-$ is the counter ion associated with the cationic center; and n is from about 10 to about 10,000. The average molecular weight of the polymers of formula (I) is from about 1 kDa to about 1,000 kDa.

Hydrolysis of the cationic polymer of formula (I) provides zwitterionic polymer having formula (II):

$$\text{PB-}(L_1\text{-}N^+(R_a)(R_b)\text{-}L_2\text{-}A(=O)O^-)_n \quad \text{(II)}$$

wherein PB, $L_1$, $N^+$, $R_a$, $R_b$, $L_2$, A, and n are as described above, and $A(=O)O$— is the anionic group.

In this embodiment, the polymer of formula (I) includes n pendant groups and can be prepared by polymerization of monomers having formula (III):

$$CH_2=C(R_d)\text{-}L_1\text{-}N^+(R_a)(R_b)\text{-}L_2\text{-}A(=O)\text{—}OR_cX^- \quad \text{(III)}$$

wherein $L_1$, $N^+$, $R_a$, $R_b$, $A(=O)OR_c$, and $L_2$, and $X^-$ are as described above, $R_d$ is selected from hydrogen, fluorine, trifluoromethyl, C1-C6 alkyl, and C6-C12 aryl groups.

The following is a description of the polymers and monomers of formulas (I)-(III) described above.

In formulas (I) and (II), PB is the polymer backbone. Representative polymer backbones include vinyl backbones (i.e., —C(R')(R'')—C(R''')(R'''')—, where R', R'', R''', and R'''' are independently selected from hydrogen, alkyl, and aryl) derived from vinyl monomers (e.g., acrylate, methacrylate, acrylamide, methacrylamide, styrene). Other suitable backbones include polymer backbones that provide for pendant cationic groups that include hydrolyzable groups that can be converted to zwitterionic groups, and backbones that include cationic groups and that provide for pendant hydrolyzable groups that can be converted to zwitterionic groups. Other representative polymer backbones include peptide (polypeptide), urethane (polyurethane), and epoxy backbones.

Similarly, in formula (III), $CH_2=C(R_d)$— is the polymerizable group. It will be appreciated that other polymerizable groups, including those noted above, can be used to provide the monomers and polymers of the invention.

In formulas (I)-(III), $N^+$ is the cationic center. In certain embodiments, the cationic center is a quaternary ammonium (N bonded to $L_1$; $R_a$, $R_b$, and $L_2$). In addition to ammonium, other useful cationic centers include imidazolium, triazaolium, pyridinium, morpholinium, oxazolidinium, pyrazinium, pyridazinium, pyrimidinium, piperazinium, and pyrrolidinium.

$R_a$ and $R_b$ are independently selected from hydrogen, alkyl, and aryl groups. Representative alkyl groups include C1-C10 straight chain and branched alkyl groups. In certain embodiments, the alkyl group is further substituted with one of more substituents including, for example, an aryl group (e.g., —$CH_2C_6H_5$, benzyl). In one embodiment, $R_a$ and $R_b$ are methyl. Representative aryl groups include C6-C12 aryl groups including, for example, phenyl. For certain embodiments of formulas (I)-(III), $R_2$ or $R_3$ is absent.

$L_1$ is a linker that covalently couples the cationic center to the polymer backbone. In certain embodiments, $L_1$ includes a functional group (e.g., ester or amide) that couples the remainder of $L_1$ to the polymer backbone (or polymerizable moiety for the monomer of formula (III)). In addition to the functional group, $L_1$ can include an C1-C20 alkylene chain. Representative $L_1$ groups include —$C(=O)O$—$(CH_2)_n$— and —$C(=O)NH$—$(CH_2)_n$—, where n is 1-20 (e.g., 3).

$L_2$ is a linker that covalently couples the cationic center to the hydrolyzable group (or anionic group for the zwitterionic polymer of formula (II)). $L_2$ can be a C1-C20 alkylene chain. Representative $L_2$ groups include —$(CH_2)_n$—, where n is 1-20 (e.g., 1, 3, or 5).

The hydrophobicity and the rate of hydrolysis of the cationic polymers of formula (I) can be controlled by $L_1$ and/or $L_2$. The greater the hydrophobicity of $L_1$ or $L_2$, the slower the hydrolysis of the hydrolyzable group and the conversion of the cationic polymer to the zwitterionic polymer.

$A(=O)$—$OR_c$ is the hydrolyzable group. The hydrolyzable group can be an ester, such as a carboxylic acid ester (A is C), a sulfinic acid ester (A is S), a sulfonic acid ester (A is SO), a phosphinic acid ester (A is P), or a phosphonic acid ester (A is PO). The hydrolyzable group can also be an anhydride. $R_c$ is an alkyl, aryl, acyl, or silyl group that may be further substituted with one or more substituents.

Representative alkyl groups include C1-C30 straight chain and branched alkyl groups. In certain embodiments, the alkyl group is further substituted with one of more substituents including, for example, an aryl group (e.g., —$CH_2C_6H_5$, benzyl). In certain embodiments, $R_c$ is a C1-C20 straight chain alkyl group. In one embodiment, $R_c$ is methyl. In another embodiment, $R_c$ is ethyl. In one embodiment, $R_c$ is a C3-C20 alkyl. In one embodiment, $R_c$ is a C4-C20 alkyl. In one embodiment, $R_c$ is a C5-C20 alkyl. In one embodiment, $R_c$ is a C6-C20 alkyl. In one embodiment, $R_c$ is a C8-C20 alkyl. In one embodiment, $R_c$ is a C10-C20 alkyl. For applications where relatively slow hydrolysis is desired, $R_c$ is a C4-C20 n-alkyl group or a C4-C30 n-alkyl group.

Representative aryl groups include C6-C12 aryl groups including, for example, phenyl including substituted phenyl groups (e.g., benzoic acid).

Representative acyl groups ($—C(=O)R_e$) include acyl groups where $R_e$ is C1-C20 alkyl or C6-C12 aryl.

Representative silyl groups ($—SiR_3$) include silyl groups where R is C1-C20 alkyl or C6-C12 aryl.

In certain embodiments of the invention, the hydrolysis product $R_cO^-$ (or $R_cOH$) is a therapeutic agent (e.g., an antimicrobial agent, such as salicylic acid (2-hydroxybenzoic acid), benzoate, lactate, and the anion form of antibiotic and antifungal drugs).

In certain other embodiments, the hydrolysis product $R_cO^-$ (or $R_cOH$) is a lactate, glycolate, or amino acid.

The rate of hydrolysis of the cationic polymers of formula (I) can also be controlled by $R_c$. The slower the hydrolysis of the hydrolyzable group due to, for example, steric and/or kinetic effects due to $R_c$, the slower the conversion of the cationic polymer to the zwitterionic polymer.

$X^-$ is the counter ion associated with the cationic center. The counter ion can be the counter ion that results from the synthesis of the cationic polymer of formula (I) or the monomers of formula (III) (e.g., $Cl^-$, $Br^-$, $I^-$). The counter ion that is initially produced from the synthesis of the cationic center can also be exchanged with other suitable counter ions to provide polymers having controllable hydrolysis properties and other biological properties.

The rate of hydrolysis of the cationic polymers of formula (I) can be controlled by the counter ion. The more hydrophobic the counter ion, the slower the hydrolysis of the hydrolyzable group and the slower the conversion of the cationic polymer to the zwitterionic polymer. Representative hydrophobic counter ions include carboxylates, such as benzoic acid and fatty acid anions (e.g., $CH_3(CH_2)_nCO_2^-$ where n=1-19); alkyl sulfonates (e.g., $CH_3(CH_2)_nSO_3^-$ where n=1-19); salicylate; lactate; bis(trifluoromethylsulfonyl)amide anion ($N—(SO_2CF_3)_2$); and derivatives thereof. Other counter ions also can be chosen from chloride, bromide, iodide, sulfate; nitrate; perchlorate ($ClO_4$); tetrafluoroborate ($BF_4$); hexafluorophosphate ($PF_6$); trifluoromethylsulfonate ($SO_3CF_3$); and derivatives thereof.

Other suitable counter ions include hydrophobic counter ions and counter ions having therapeutic activity (e.g., an antimicrobial agent, such as salicylic acid (2-hydroxybenzoic acid), benzoate, lactate, and the anion form of antibiotic and antifungal drugs).

For the monomer of formula (III), $R_d$ is selected from hydrogen, fluoride, trifluoromethyl, and C1-C6 alkyl (e.g., methyl, ethyl, propyl, butyl). In one embodiment, $R_d$ is hydrogen. In one embodiment, $R_d$ is methyl. In another embodiment, $R_d$ is ethyl.

The variation of the structural features of the cationic polymers allows for their controlled hydrolysis and the control of the biological, chemical, and mechanical properties. The structural features of the cationic polymers noted above that can be varied to achieve the desired controlled hydrolysis of the polymer include $L_1$, $L_2$, $R_a$, $R_b$, A, $R_c$, and $X^-$. In general, the more hydrophobic the polymer or the noted structural feature, the slower the hydrolysis of the cationic polymer to the zwitterionic polymer.

Homopolymers, Random Copolymers, Block Copolymers. The cationic polymer of the invention include homopolymers, random copolymers, and block copolymers.

In one embodiment, the invention provides cationic homopolymers, such as defined by formula (I), prepared by polymerizing a cationic monomer, such as defined by formula (III). It will be appreciated that the advantageous properties associated with cationic polymers of the invention including those polymers defined by formula (I) can be imparted to other polymeric materials.

In one embodiment, the invention provides random copolymers prepared by copolymerizing two different cationic monomers of formula (III).

In another embodiment, the invention provides random copolymers that include cationic repeating units prepared by copolymerizing one or more cationic monomers of the invention defined by formula (III) with one or more other monomers (e.g., hydrophobic monomers, anionic monomers, or zwitterionic monomers, such as phosphorylbetaine, sulfobetaine, or carboxybetaine monomers).

In one embodiment, the invention provides block copolymers having one or more blocks comprising cationic repeating units and one or more other blocks. In this embodiment, the one or more blocks that include cationic repeating units include only cationic repeating units (e.g., homo- or copolymer prepared from cationic monomers of formula (III)). Alternatively, the one or more blocks that include cationic repeating units include cationic repeating units and other repeating units (e.g., hydrophobic, anionic, zwitterionic repeating units).

Other Suitable Polymers

The invention also provides the following polymers.

In one embodiment, the cationic polymer has the following structure:

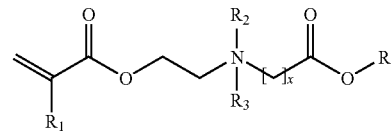

$R_1$=—H, —$CH_3$, —$C_2H_5$ $R_2$=no atom, —H, —$CH_3$, —$C_2H_5$ $R_3$=—H, —$CH_3$, —$C_2H_5$ x=1-8.

R=any alkyl chain, aromatic or lactate or glycolate

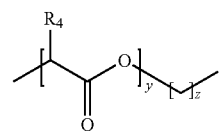

$R_4$=—H, —$CH_3$, —$C_2H_5$

Y=1-10

Z=0-22 or C(=O)R' R'=any alkyl chain or aromatic group.

In another embodiment, the cationic polymer has the following structure:

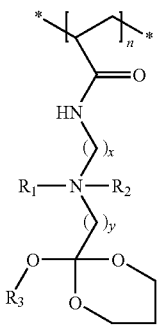

n>5
x=1-5
y=1-5
$R_1$=H, or alkyl chain
$R_2$=no atom, H, or alkyl chain
$R_3$=alkyl chain.

In another embodiment, the invention provides a polymer having the following structure:

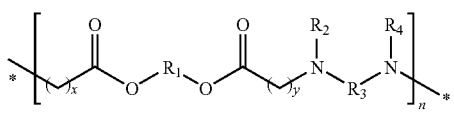

$R_1$ is any alkyl chain
$R_3$ is any alkyl chain
$R_2$, $R_4$ is any alkyl chain
x=1-18
y=1-18
n>3.

In another embodiment, the invention provides a polymer having the following structure:

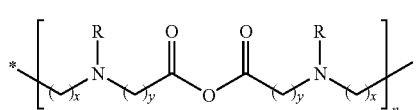

R is alkyl chain
x=1-18
y=1-18
n>3.

In another embodiment, the invention provides a polymer having the following structure:

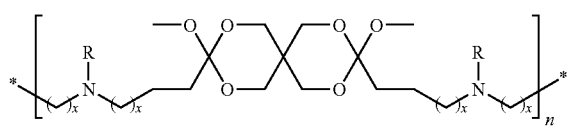

R=any alkyl chain
x=0-11
n>3.

In another embodiment, the invention provides a polymer having the following structure:

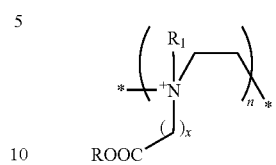

n>3x
x=1-10
R=any alkyl chain, aromatic or lactate or glycolate.

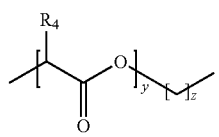

$R_4$=—H, —$CH_3$, —$C_2H_5$
y=1-10
z=0-22
or C(=O)R'
R'=any alkyl chain, aromatic group.

In another embodiment, the invention provides polymers having the following structure:

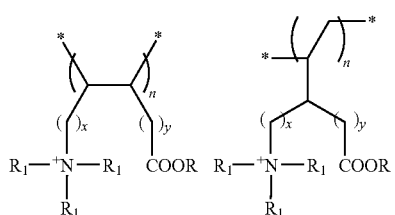

n>3
x=1-6
y=0-6
R=any alkyl chain, aromatic or lactate or glycolate)

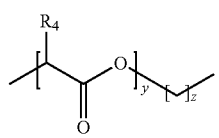

$R_4$=—H, —$CH_3$, —$C_2H_5$
y=1-10
z=0-22
or C(=O)R'
R=any alkyl chain, aromatic group.

In another embodiment, the invention provides a polymer having the following structure:

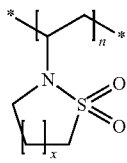

n>5
x=0-5.

In another embodiment, the invention provides a polymer having the following structure:

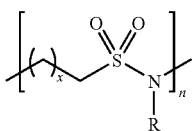

x=0-17
n>5
R=H or alkyl chain.

In another embodiment, the invention provides a polymer having the following structure:

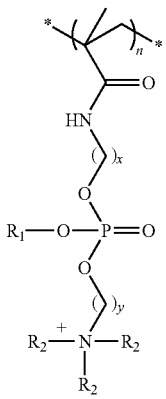

n>5
$R_2$=H or any alkyl chain, e.g., methyl
x, y=1-6
$R_1$=any alkyl chain,

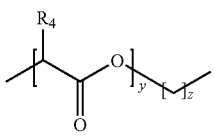

$R_4$=—H, —$CH_3$, —$C_2H_5$
y=1-10
z=0-22

In another embodiment, the invention provides a polymer having the following structure:

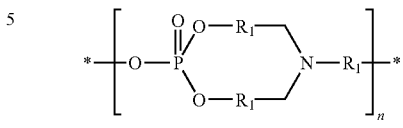

n>3
$R_1$=any alkyl chain.

Three representative cationic monomers of formula (III) useful for making cationic polymers of formula (I), and ultimately the zwitterionic polymers of formula (II) are illustrated in FIG. 1. Referring to FIG. 1, three positively charged polyacrylamides having pendant groups that bear cationic carboxybetaine ester groups are illustrated. The three monomers have different spacer groups ($L_2$: —$CH_2$)$_n$—) between the quaternary ammonium groups (cationic center) and the ester (hydrolyzable) groups: CBAA-1-ester (n=1); CBAA-3-ester (n=3); and CBAA-5-ester (n=5). Polymerization of the monomers provides the corresponding cationic polymers. The three monomers were polymerized using free radical polymerization to form linear polymers, or using surface-initiated ATRP to prepare polymer brushes on SPR sensors. The polymers with different spacer groups ($L_2$) and ester groups were expected to have different chemical, physical and biological properties. The synthesis of the three monomers and their polymerizations are described in Example 1.

Figure 2:
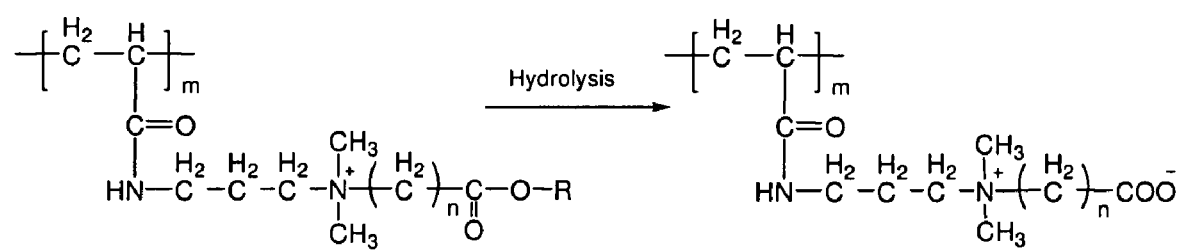
FIG. 2 illustrates the hydrolysis of a representative cationic polymer of the invention: hydrolysis of a cationic polycarboxybetaine ester to zwitterionic polycarboxybetaine.
Figure 3:
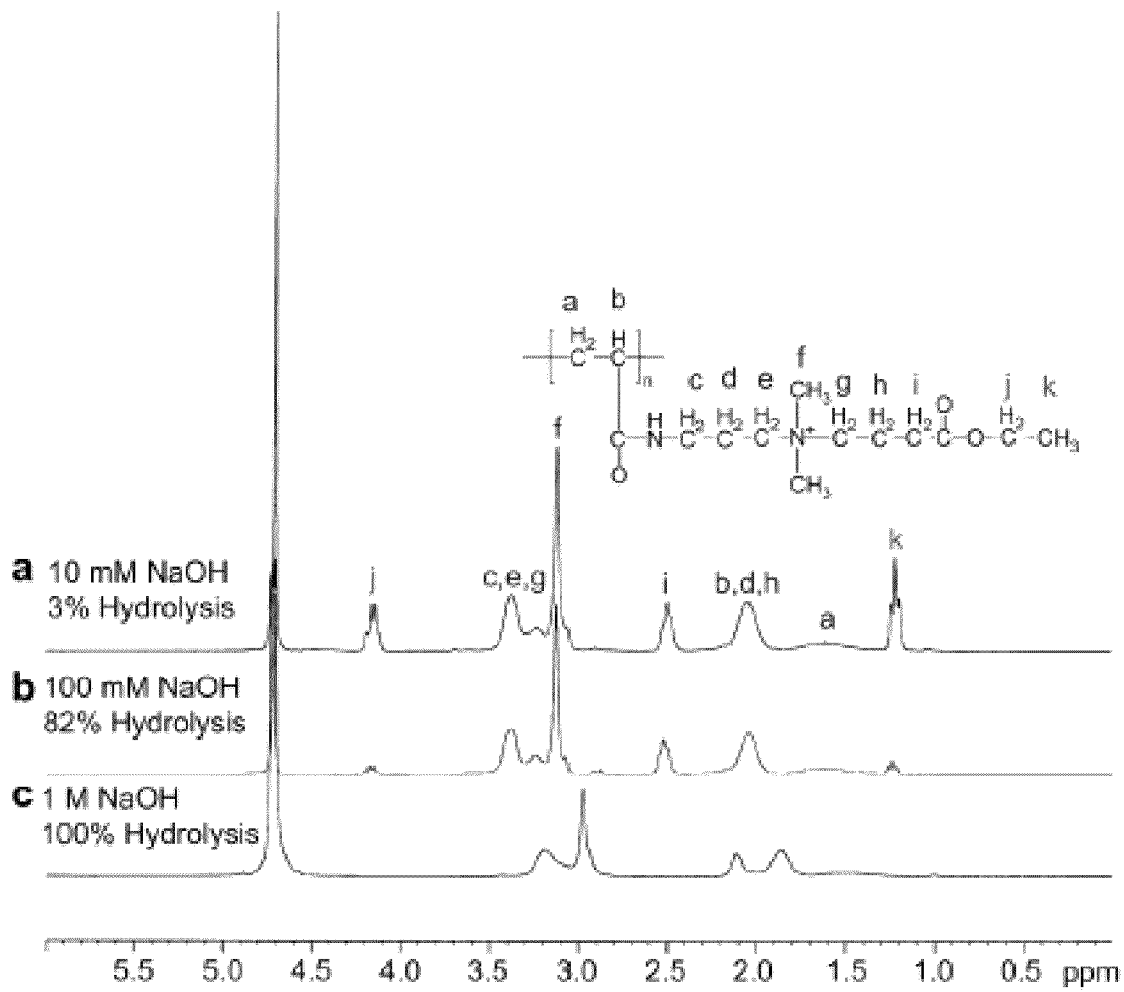
FIG. 3 compares the $^1H$ NMR spectra of the hydrolysis of a representative cationic polymer of the invention, polyCBAA-3-ester, after one-hour treatment in a solution with the sodium hydroxide concentration of (a) 10 mM (3% hydrolysis), (b) 100 mM (82% hydrolysis), and (c) 1 M (100% hydrolysis).
Figure 4:
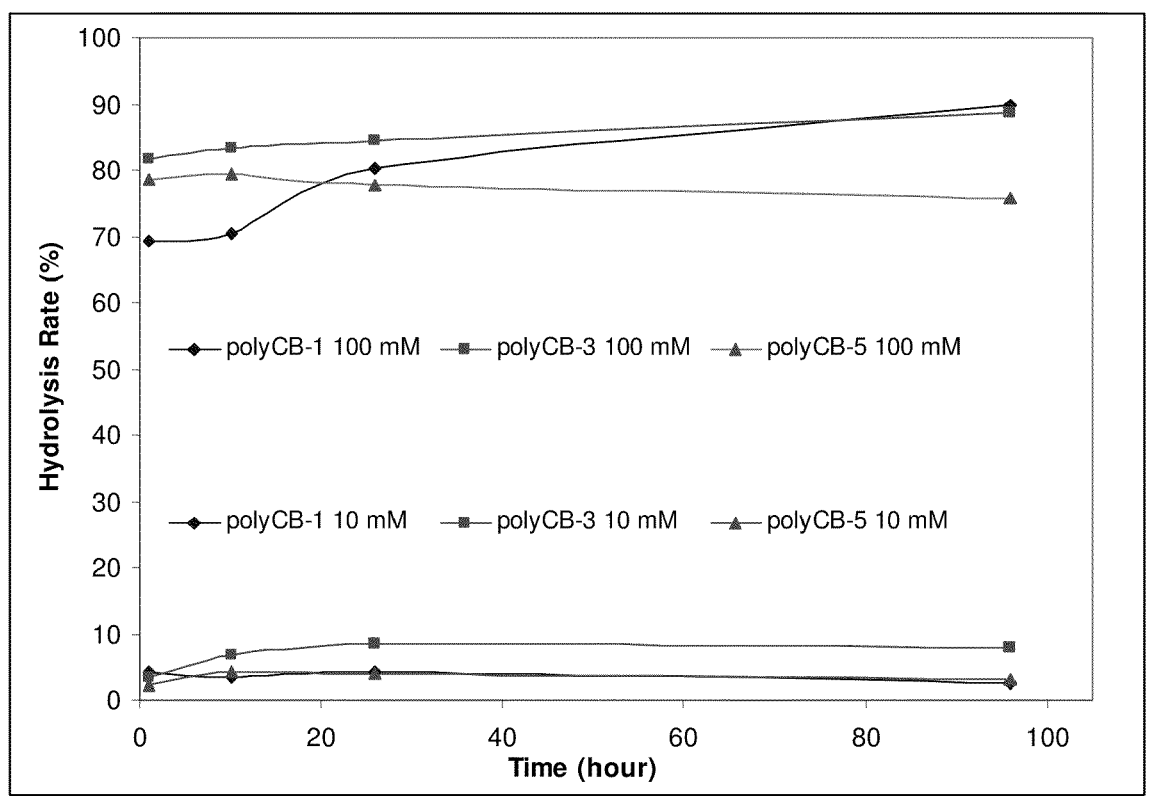
FIG. 4 compares the hydrolysis rates of representative cationic polymers of the invention at 10 mM and 100 mM aqueous sodium hydroxide.

For the linear polymers polymerized via free radical polymerization, their molecular weights were measured using gel permeation chromatography (GPC) in aqueous solutions. PolyCBAA-1-ester, polyCBAA-3-ester, and polyCBAA-5-ester had average molecular weights of 14 kDa, 13 kDa, and 9.6 kDa, respectively Hydrolysis of the cationic polymers provides the zwitterionic polymers (i.e., zwitterionic polycarboxybetaines). The hydrolysis of representative cationic polymer of the invention is described in Example 2 and illustrated schematically in FIG. 2. In FIG. 2, n is 1, 3, or 5 (corresponding to polyCBAA-1-ester, polyCBAA-3-ester, and polyCBAA-5-ester, respectively). The three carboxybetaine ester polymers were dissolved under different sodium hydroxide concentrations and their hydrolysis behavior was studied. After a period of time, the hydrolysis rate of the polymers was analyzed by measuring the retaining ester groups on the polymer using $^1$H NMR. All the three polymers are stable in water and no evident hydrolysis was detected after four days. The concentration of NaOH is crucial for the hydrolysis of the carboxybetaine ester polymers. FIG. 3 illustrates the NMR spectra of polyCBAA-3-ester after a one-hour treatment with three different concentrations of NaOH. For NaOH solution with a concentration of 10 mM, only slightly hydrolysis was detected (ca. 3%). For 100 mM NaOH solution, about 82% polymer was hydrolyzed. For the NaOH concentration of 1 M, the polymer was totally hydrolyzed in one hour. FIG. 4 graphs the hydrolysis rate under 100 mM or 10 mM NaOH as a function of time. Referring to FIG. 4, under these two NaOH concentrations, most hydrolysis happens in the first hour. After that, the hydrolysis rate changes only slightly with the time.

As noted above, the hydrolysis rate of the cationic polymers of the invention can be controlled by modifying their structures. To obtain the different hydrolysis behavior, cationic polymers having varying structure parameters such as ester groups (hydrolyzable groups), spacer groups ($L_1$ and $L_2$), and counter ions ($X^-$). Hydrolysis behavior can also be controlled by varying polymer molecular weight or copolymerizing with other monomers. Hydrolyzable ester groups (such as t-butyl and alkyl substituted silyl) or anhydride groups can be easily hydrolyzed under acidic or basic condition. Changing spacer groups ($L_2$: —$CH_2$)$_n$—) between the quaternary ammonium groups (cationic center) and the ester (hydrolyzable) groups also can tune the hydrolysis rate. Short spacers can increase the hydrolysis rate. In addition, counter ions, such as hydrophilic anions (e.g., $Cl^-$, $Br^-$, $I^-$, $SO_4$) also increase the hydrolysis rate, and low polymer molecular weight and copolymerization with other hydrophilic monomers also help to increase the hydrolysis rate.

Protein Adsorption

The hydrolyzable cationic polymers of the invention can advantageously be used as materials effective in reducing protein adsorption to surfaces treated with the polymers. The cationic polymers can be used to prepare low-fouling surfaces. These surfaces can be advantageously employed for devices in environments where the protein adsorption to device surfaces are detrimental.

To demonstrate the utility of representative cationic polymers of the invention in providing surfaces having low protein adsorption, polymer brushes were prepared from representative cationic polymers as described in Example 3 and their protein adsorption measured.

The three monomers (CBAA-1-ester, CBAA-3-ester, and CBAA-5-ester) were grafted on the surfaces of a SPR sensor using surface-initiated ATRP. The polymer brushes had a thickness of 5-20 nm estimated from XPS analysis. Protein adsorption from a 1 mg/mL fibrinogen solution on the three polymer brushes was measured using SPR. Fibrinogen is a sticky protein and plays an important role in platelet aggregation and blood clotting on biomaterials. Fibrinogen adsorption was 195 ng/cm$^2$, 255 ng/cm$^2$, and 600 ng/cm$^2$ for polyCBAA-1-ester, polyCBAA-3-ester, and polyCBAA-5-ester, respectively (see FIGS. 5A-5C). All three polymers have evident protein adsorption due to their positive charges. PolyCBAA-1-ester had relatively lower fibrinogen adsorption due to its higher hydrophilicity compared to the other two esters having more hydrophobic $L_2$ (i.e., C3 and C5, respectively). With the increase in $L_2$ from methylene to propylene to pentylene, the hydrophobicity of the polymer increases, leading to higher fibrinogen adsorption.

Figure 5A:
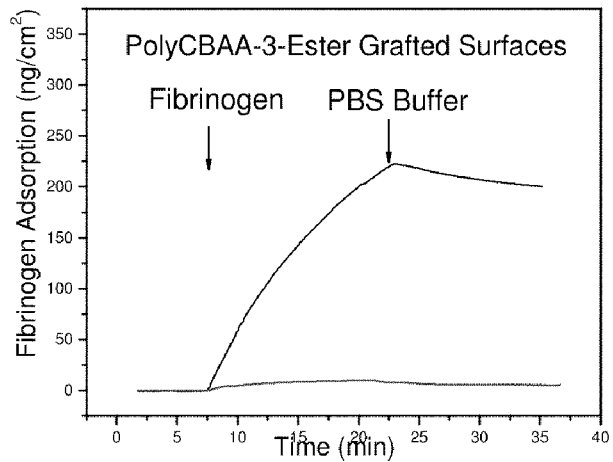
FIGS. 5A-5C are SPR sensorgrams for fibrinogen adsorption on the surfaces grafted with representative polymers of the invention: polycarboxybetaine esters before and after hydrolysis; (a) polyCBAA-1-ester, (b) polyCBAA-3-ester, and (c) polyCBAA-5-ester. The surfaces with polymer brushes were hydrolyzed with a 100 mm NaOH solution for 1-2 h.
Figure 5B:
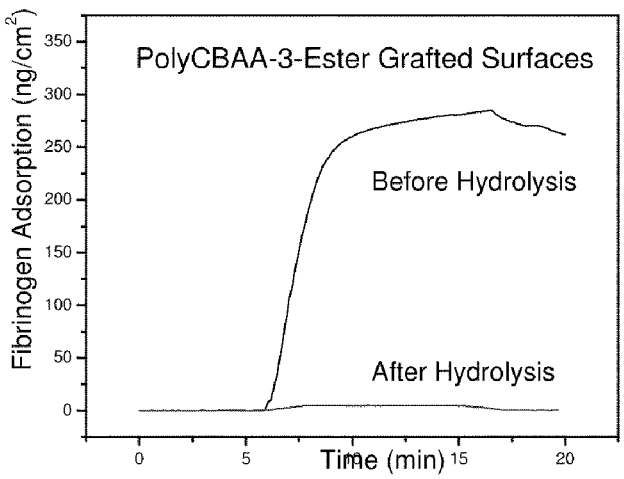
Figure 5C:
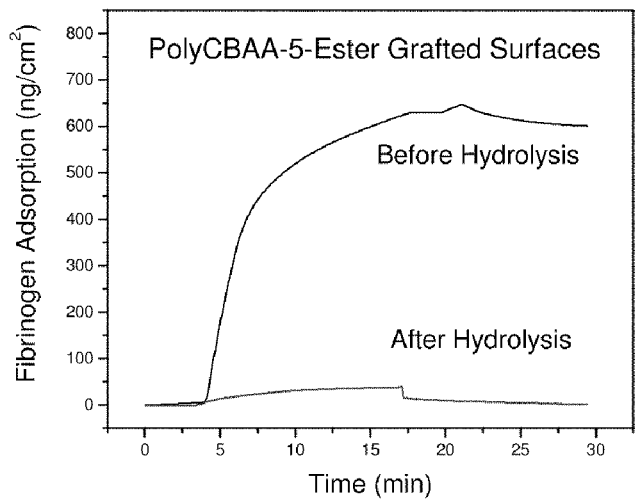

After hydrolysis at 100 mM for 1-2 hours, surface properties were dramatically changed. FIGS. 5A-5C illustrate that the surfaces grafted with each of the three polymers were converted to surfaces that were highly resistant to fibrinogen adsorption. On the surfaces with hydrolyzed polyCBAA-1-ester and hydrolyzed polyCBAA-3-ester, fibrinogen adsorption is less than 0.3 ng/cm$^2$, which is the detection limit of the SPR. Fibrinogen adsorption on hydrolyzed polyCBAA-5-ester was about 1.5 ng/cm$^2$. By controlling hydrolysis, the polymer-grafted surfaces can change their properties from high protein adsorption to strongly resistant to protein adsorption. Moreover, resulting surfaces with zwitterionic polymers after hydrolysis are biocompatible and highly resistant to nonspecific protein adsorption from blood plasma/serum and bacterial adhesion/biofilm formation.

Antimicrobial Properties

The hydrolyzable cationic polymers of the invention exhibit antimicrobial properties. The evaluation of antimicrobial properties of representative cationic polymers of the invention is described in Example 4.

To evaluate the antimicrobial properties of the cationic polycarboxybetaine esters, polymer solutions of polyCBAA-1-ester, polyCBAA-3-ester, and polyCBAA-5-ester were incubated with *E. coli*. It was found that at a concentration of 2 mM (repeat unit molar concentration), polyCBAA-1-ester, polyCBAA-3-ester, and polyCBAA-5-ester present a live cell percentage of 95%, 87.3%, and 46.2%, respectively (see FIG. 6). Antimicrobial activities appears to increase with the increase in the length of $L_2$. After hydrolysis, the zwitterionic polymers, polyCBAA-1, polyCBAA-3, and polyCBAA-5, exhibit a live cell percentage of 93.7%, 96.3% and 95.3%, respectively, indicating that the antimicrobial activity decreases with the hydrolysis of the cationic polymers (i.e., polycarboxybetaine esters) to the zwitterionic polymers (i.e., polycarboxybetaines).

Several amphiphilic polycations have been investigated for their antibacterial activities. The alkyl pendent chain length of the polycations was studied to compare the bactericidal efficiency of different polycations. It is found that the polymers with quaternary amine groups and longer hydrophobic pendant chains have better antimicrobial activities due to higher hydrophobicity. Small molecular quaternary ammonium compounds (QMCs) with carboxybetaine esters were found to have rapid bactericidal action when they have longer hydrocarbon groups. These QMCs could bind to the outer membrane and cytoplasmic membrane of enterobacteria and permeate into the bacterial membranes. The antimicrobial effect is increased with increasing the spacer length ($L_2$) of the cationic polymers (e.g., polycarboxybetaine esters) of the invention.

The antimicrobial efficacy of the polyCBAA-5-ester is comparable to that of other quaternized polymers with similar alkyl chain length. Higher antimicrobial efficacy can be achieved with longer alkyl chain lengths (e.g., C1-C20).

For conventional antimicrobial coatings, the killed microbes and adsorbed proteins usually accumulate on the surfaces and dramatically decrease their antimicrobial activities. In contrast, antimicrobial coatings made from the cationic polymers of the invention are hydrolyzed to zwitterionic polymers to provide surfaces that are highly resistant to the adsorption of various biomolecules. These zwitterionic polymers are nontoxic, biocompatible, and nonfouling, both as bulk materials and surface coatings.

Representative crosslinked zwitterionic polymers of the invention, polycarboxybetaines hydrogels, were non-cytotoxic and contain less than 0.06 units (EU)/mL of endotoxin using a *Limulus Amebocyte* Lysate (LAL) endotoxin assay kit (Cambrex Bioscience. Walkerville, Md.). The polycarboxybetaine hydrogels were implanted subcutaneously within mice for up to four weeks. The results showed that the polycarboxybetaines have in vivo biocompatibility comparable to that of poly(2-hydroxyethyl methacrylate (polyHEMA) hydrogels, a well-accepted model biomaterial for implantation. The nontoxic properties of the zwitterionic polymers convert the toxicity of their cationic polymer precursors and further provide nonfouling properties that can prevent dead microbes and adsorbed proteins from accumulating on the surface.

Switchable Polymer Coatings and their Use in Medical Devices

The cationic polymers of the invention, hydrolyzable to zwitterionic polymers, can be advantageously used as coatings for the surfaces of a variety of devices including, for example, medical devices. In this embodiment, the cationic polymers of the invention provide switchable biocompatible polymer surfaces having self-sterilizing and nonfouling capabilities.

Figure 7:
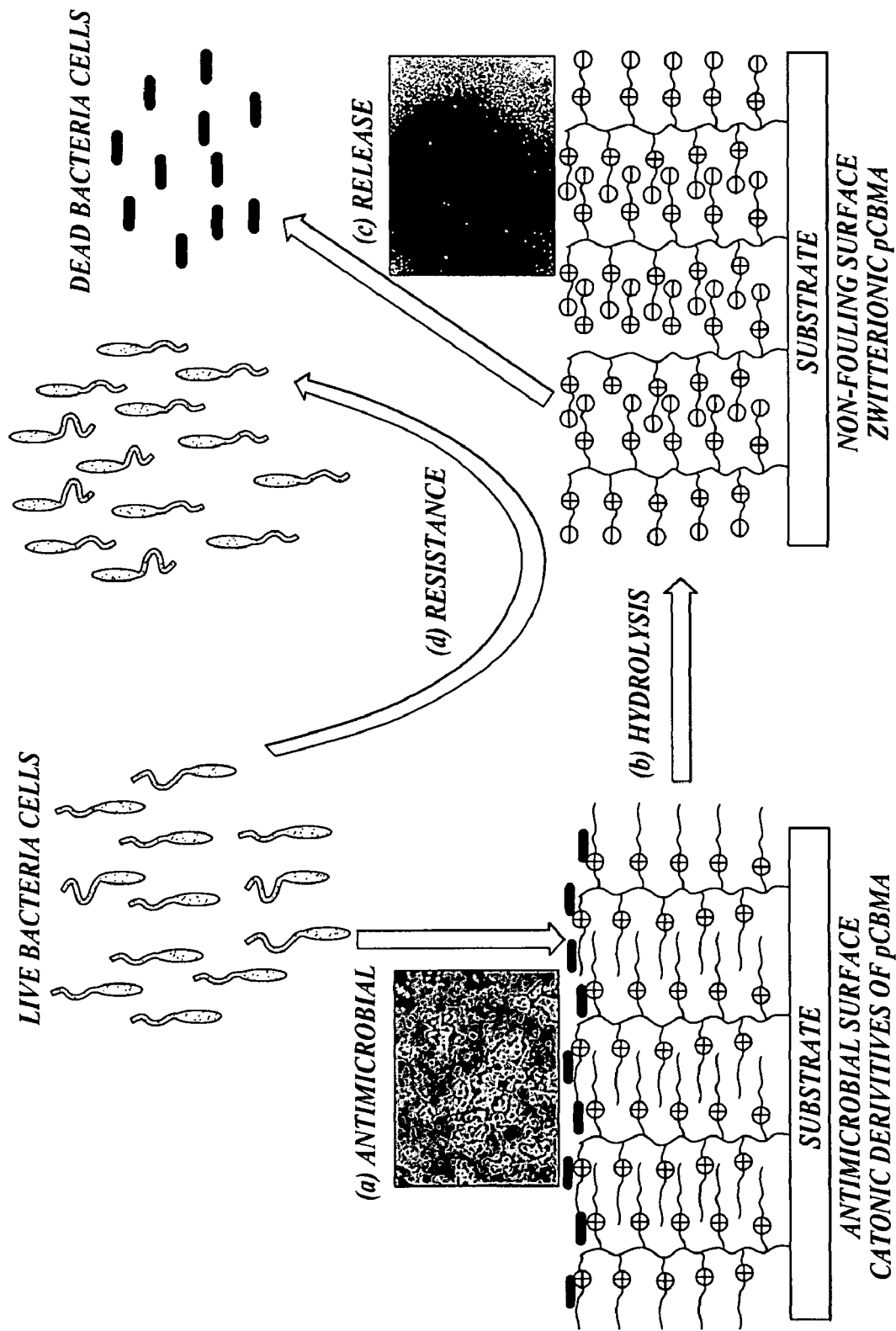
FIG. 7 is a schematic illustration of a representative surface of the invention coated with a cationic polymer. The surface switches from an antibacterial surface to a non-fouling surface upon hydrolysis: (a) antimicrobial cationic pCBMA-1 C2 effectively kills bacteria, (b) pCBMA-1 C2 is converted to non-fouling zwitterionic pCBMA-1 upon hydrolysis, (c) killed bacteria remaining on the surface is released from non-fouling zwitterionic pCBMA-1 demonstrating that (d) zwitterionic pCBMA-1 itself is highly resistant to bacterial adhesion.
Figure 8:
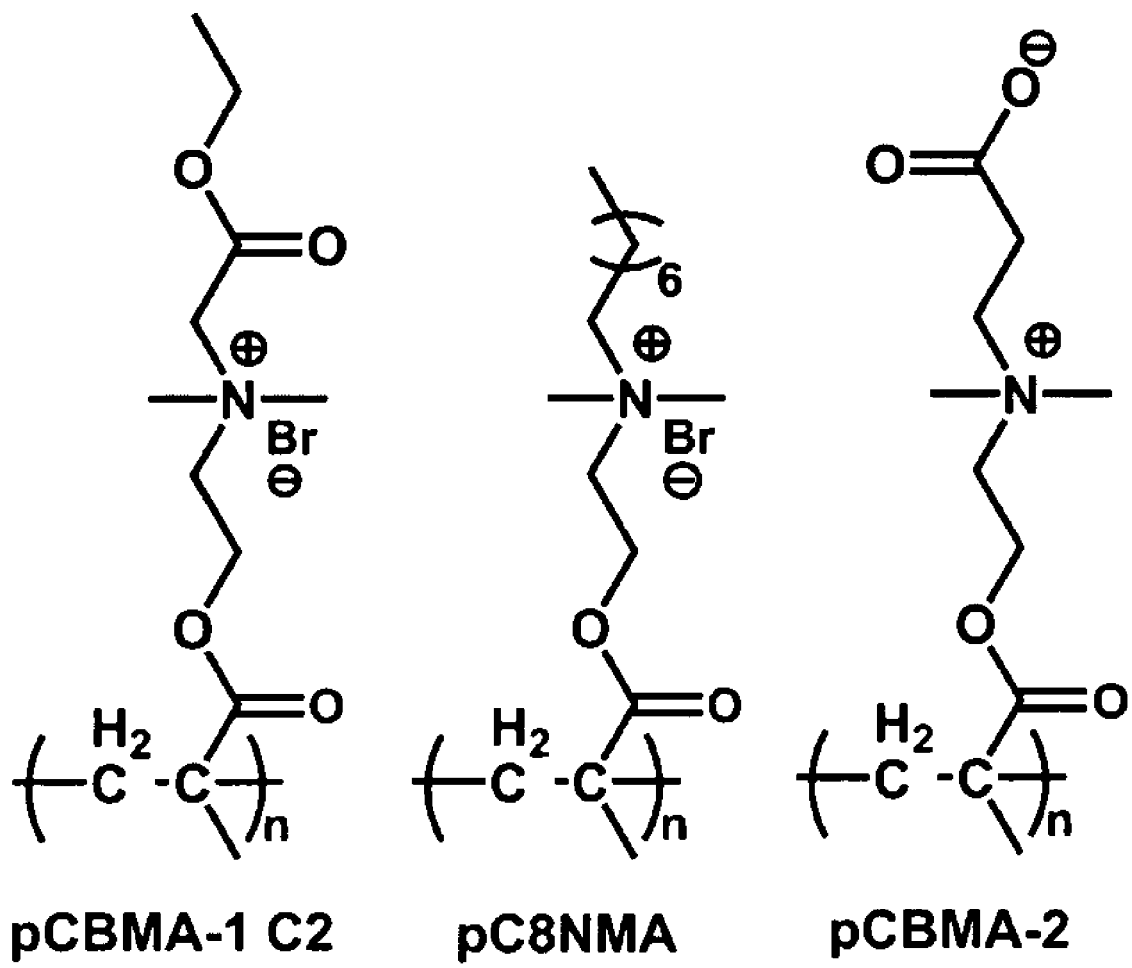
FIG. 8 illustrates the chemical structures of a representative cationic polymer of the invention, switchable pCBMA-1 C2; antimicrobial cationic pC8NMA; and non-fouling zwitterionic pCBMA-2.

FIG. 7 is a schematic illustration of a switchable biocompatible polymer surfaces having self-sterilizing and nonfouling capabilities. Referring to FIG. 7, antimicrobial surface (a) is a surface coated with a representative cationic polymer of the invention (i.e., pCBMA-1 C2, see FIG. 8) that effectively kills bacteria. On hydrolysis (b) the representative cationic polymer is converted to a nonfouling zwitterionic polymer (i.e., pCBMA-1, the carboxylate corresponding to pCBMA-1 C2 ester) and dead bacteria remaining on the surface are released (c) from the nonfouling zwitterionic polymer (i.e., pCBMA-1) to provide a surface coated with the zwitterionic polymer, which is highly resistant to bacterial adhesion (d).

The materials of the invention (e.g., polymers, hydrogels) are advantageously used to coat surfaces to provide biocompatible, antimicrobial, and nonfouling surfaces. Accordingly, in another aspect, the invention provides devices and materials having a surface (i.e., one or more surfaces) to which have been applied (e.g., coated, covalently coupled, ionically associated, hydrophobically associated) one or more materials of the invention. Representative devices that may be advantageously treated with a material of the invention, modified to include a material of the invention, or incorporates a material of the invention include:

particle (e.g., nanoparticle) having a surface treated with, modified to include, or incorporates a material of the invention; drug carrier having a surface treated with, modified to include, or incorporates a material of the invention;

non-viral gene delivery system having a surface treated with, modified to include, or incorporates a material of the invention;

biosensor having a surface treated with, modified to include, or incorporates a material of the invention;

devices for bioprocesses or bioseparations, such as membranes for microbial suspension, hormone separation, protein fractionation, cell separation, waste water treatment, oligosaccharide bioreactors, protein ultrafiltration, and diary processing having a surface treated with, modified to include, or incorporates a material of the invention;

implantable sensor having a surface treated with, modified to include, or incorporates a material of the invention;

subcutaneous sensor having a surface treated with, modified to include, or incorporates by a material of the invention;

implant, such as a breast implant, cochlear implant, and dental implant having a surface treated with, modified to include, or incorporates a material of the invention;

contact lens having a surface treated with, modified to include, or incorporates a material of the invention;

tissue scaffold having a surface treated with, modified to include, or incorporates a material of the invention;

implantable medical devices, such as an artificial joint, artificial heart valve, artificial blood vessel, pacemaker, left ventricular assist device (LVAD), artery graft, and stent having a surface treated with, modified to include, or incorporates a material of the invention; and medical devices, such as an ear drainage tube, feeding tube, glaucoma drainage tube, hydrocephalous shunt, keratoprosthesis, nerve guidance tube, urinary catheter, tissue adhesive, and x-ray guide having a surface treated with, modified to include, or incorporates by a material of the invention.

Microbial adhesion onto implanted biomaterials and the subsequent formation of biofilms is one of the major causes of biomedical device failure. The use of antimicrobial and nonfouling coatings are two strategies for the prevention of the attachment and spreading of microorganisms on the surfaces of implantable materials. Antimicrobial surfaces containing covalently linked quaternary ammonium compounds (QACs) have proved to be able to efficiently kill a variety of microorganisms. A major problem with QAC surfaces is the attachment of dead microorganisms remaining on antimicrobial coatings, which can trigger an immune response and inflammation, and block its antimicrobial functional groups. In addition, such antimicrobial coatings can not fulfill the requirements of nonfouling and biocompatibility as implantable biomaterials. Poly(ethylene glycol) (PEG) derivatives or zwitterionic polymers have been extensively used as nonfouling materials to reduce bacterial attachment and biofilm formation. However, the susceptibility of PEG to oxidation damage has limited its long-term application in complex media. Zwitterionic materials such as poly(sulfobetaine methacrylate) (pSBMA) are able to dramatically reduce bacterial attachment and biofilm formation and are highly resistant to nonspecific protein adsorption, even from undiluted blood plasma and serum. Although zwitterionic coatings can reduce the initial attachment and delay colonization of microbes on surfaces, there is a possibility of introducing pathogenic microbes into the patient during implantation operations and catheter insertions, which results in the failure of implanted devices; the use of antimicrobial agents will then be necessary to eliminate these microbes. Surface-responsive materials have been developed for a broad spectrum of applications, but it is still a great challenge to develop biocompatible materials that have both antimicrobial and nonfouling capabilities.

As noted above, in one embodiment, the present invention provides a switchable polymer surface coating that combines the advantages of both nonfouling surface and that can kill greater than 99.9% of *Escherichia coli* K12 in one hour, with 98% of the dead bacterial cells released when the cationic derivatives are hydrolyzed to nonfouling zwitterionic polymers. pCBMA-1-C2 (cationic polymer of formula (I) where $L_1$ is $-C(=O)OCH_2CH_2-$, $L_2$ is $-CH_2-$, $R_c$ is $CH_2CH_3$, and $X^-$ is $Br^-$) control coatings were grafted by surface-initiated atom transfer radical polymerization (ATRP) onto a gold surface covered with initiators. The thicknesses of the obtained polymer coatings, as measured by atomic force microscopy (AFM), were 26-32 nm (Table 1).

TABLE 1

Film thicknesses (av ± std dev.) of pCBMA-1 C2, pC8NMA, and pCBMA-2 grafted onto gold-coated glass slides by ATRP and fibrinogen adsorption on these surfaces measured by SPR before and after hydrolysis under different conditions.

|  | pCBMA-1 C1 | pC8NMA | pCBMA-2 |
| --- | --- | --- | --- |
| polymer brush thickness (nm) | (31.2 ± 2.4) | (27.8 ± 2.8) | (26.1 ± 2.5) |
| protein adsorption (ng cm$^{-2}$) | | | |
| 0 h | 229.2 | 243.4 | 1.5 |
| 24 h H$_2$O | 189.9 | — | — |
| 24 h CHES (pH 9.0) | 114.9 | — | — |
| 24 h CAPS (pH 10.0) | 0 | 285.1 | 0.7 |

Figure 9:
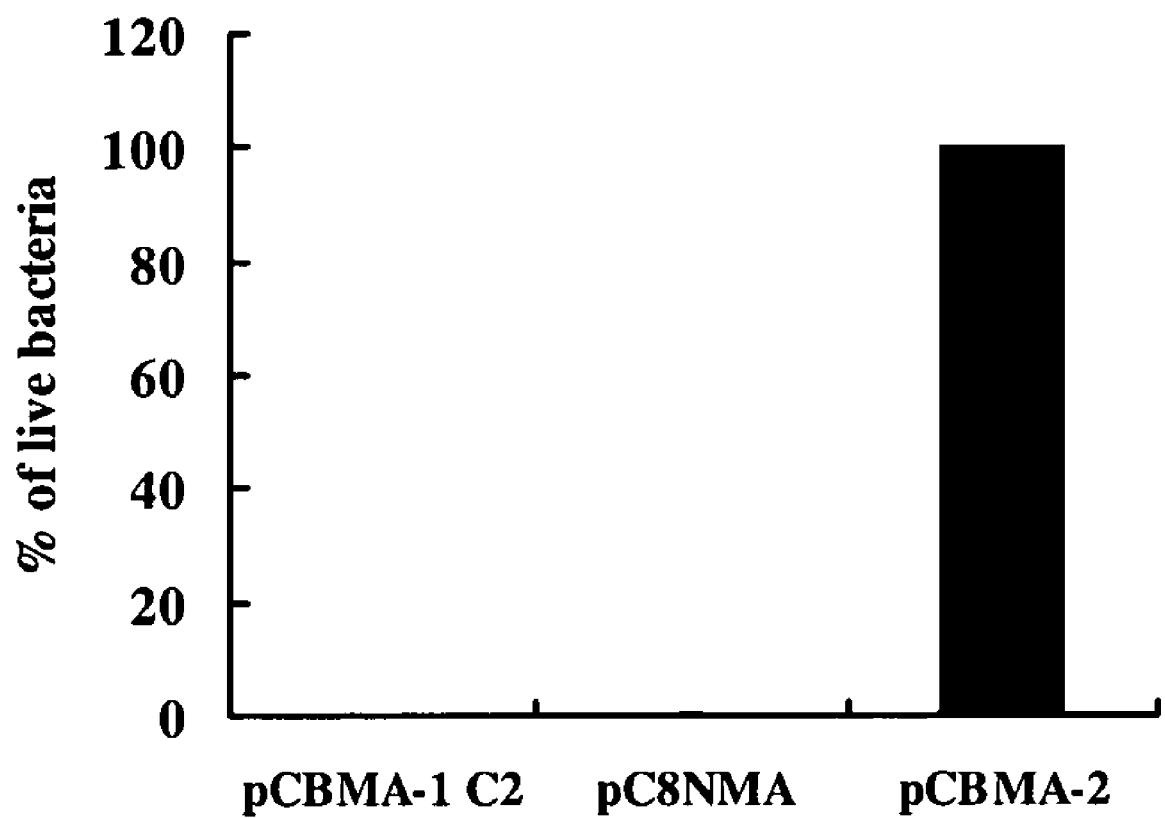
FIG. 9 is a graph comparing bactericidal activity of pCBMA-1 C2 and pC8NMA against $E.\ coli$ K12. The percentage of live $E.\ coli$ K12 colonies that grew on the surfaces coated with antimicrobial polymers is relative to the number of colonies that grew on the pCBMA-2 control (n=3).
Figures 10A, 10B, 10C, 10D, 10E, 10F:
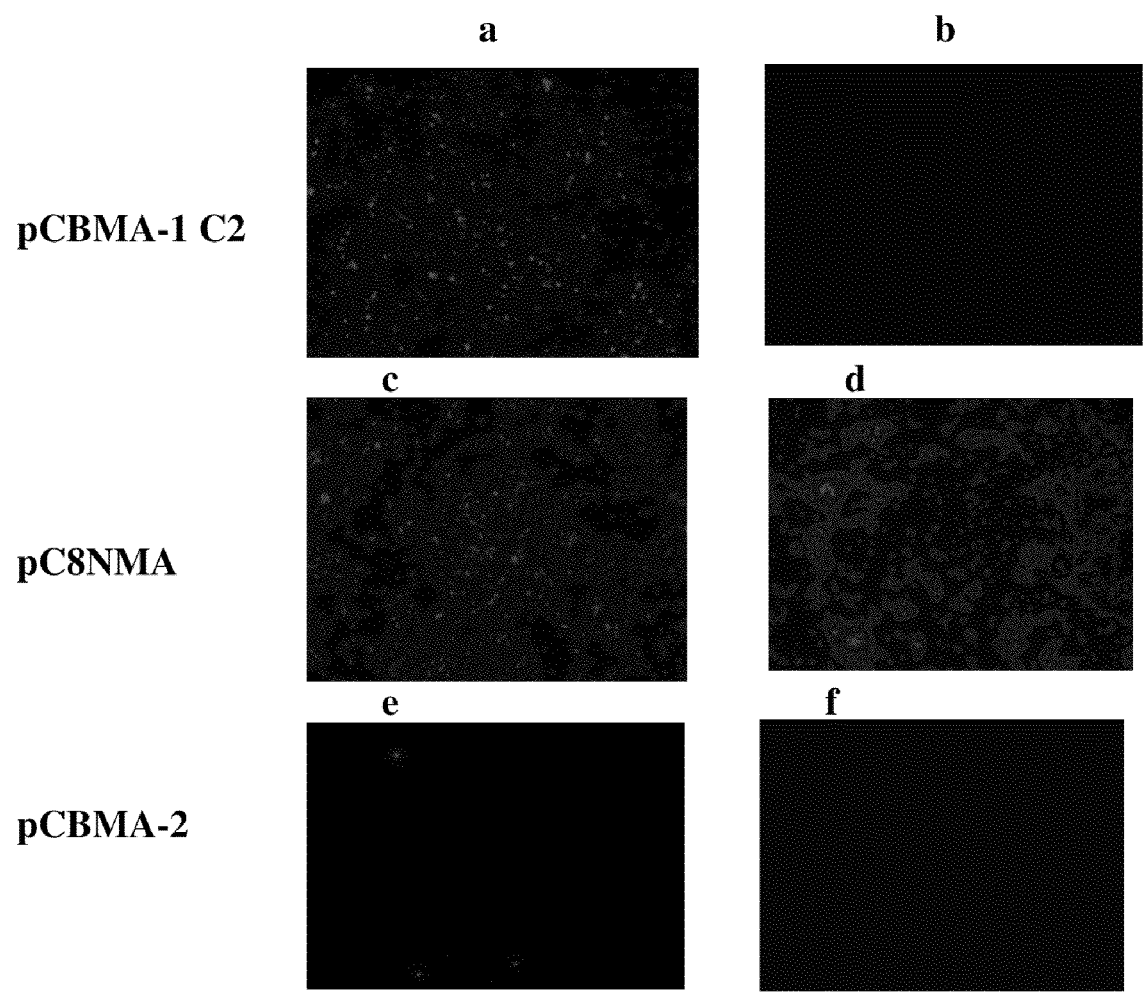
FIGS. 10A-10F are fluorescence microscopy images of attached $E.\ coli$ K12 cells (red color) from a suspension with $10^{10}$ cellsmL$^{-1}$ for one-hour exposure to the surfaces covered with various polymers: (a), (c), and (e) are for pCBMA-1 C2, pC8NMA pCBMA-2, respectively, before hydrolysis and (b), (d), and (f) are for the same polymers, respectively, after hydrolysis. Hydrolysis was for 8 days with 10 mM CAPS (pH 10.0).

The bactericidal activity of pCBMA-1 C2 surfaces was determined using *E. coli* K12, according to a modified literature procedure (Tiller et al., *Proc. Natl. Acad. Sci. USA* 98:5981, 2001). The permanently cationic poly(methacryloyloxyethyl-dimethyloctylammonium bromide) (pC8NMA, cationic control, (see FIG. 8) and the zwitterionic poly(2-carboxy-N,N-dimethyl-N-[2'-(methacryloyloxy)ethyl]ethanaminium) (pCBMA-2, zwitterionic control, see FIG. 8) were used as the positive and the negative control surfaces, respectively. The antimicrobial efficiency was defined as the amount of live cells on the tested surfaces relative to those on the pCBMA-2 surface. FIG. 9 shows that pCBMA-1 C2 and pC8NMA surfaces kill greater than 99.9% and 99.6%, respectively, of the *E. coli* in one hour relative to pCBMA-2 surfaces. The total number of live bacterial cells on the gold surface, which was also used as a negative-control surface, is similar to that on the pCBMA-2 surface.

Figure 11:
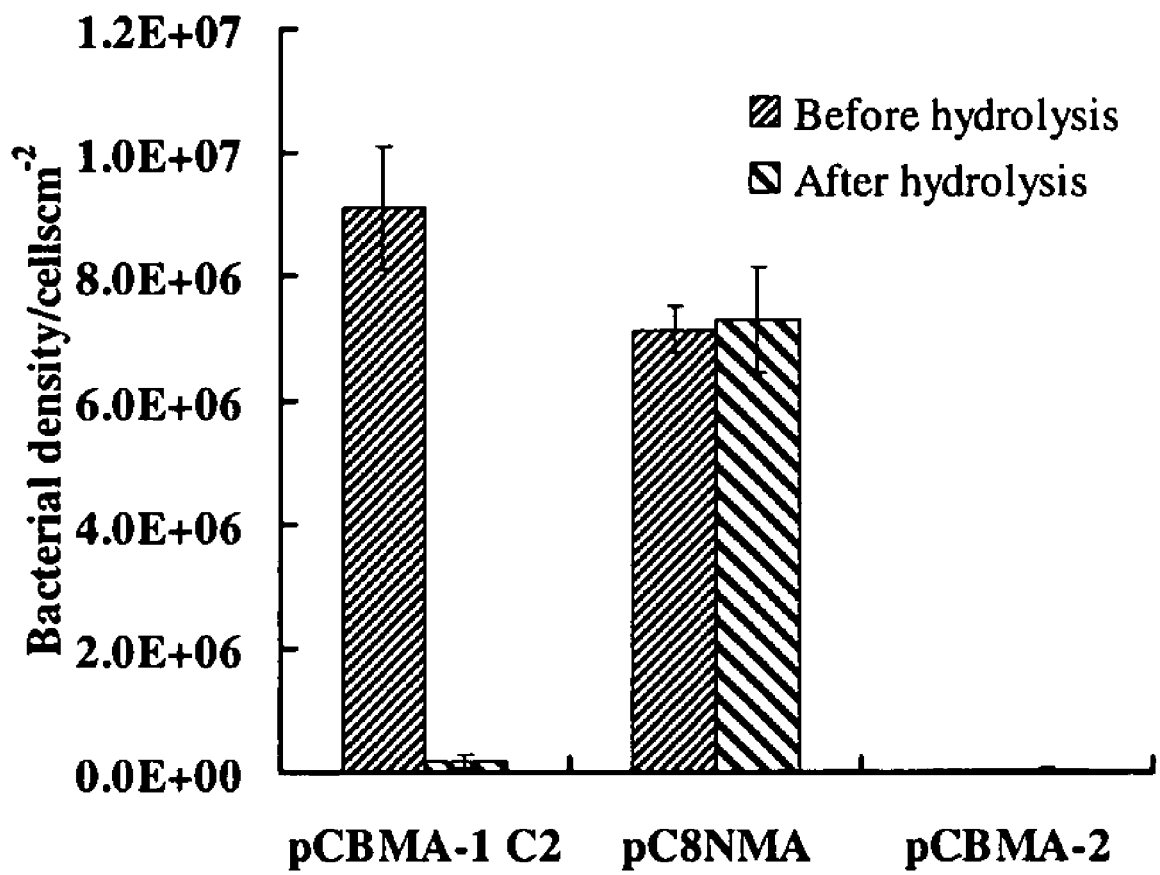
FIG. 11 is a graph comparing the attachment of $E.\ coli$ K12 from a suspension with $10^{10}$ cells mL$^{-1}$ for one-hour exposure to pCBMA-1 C2, pC8NMA, and pCBMA-2 before and after hydrolysis (n=3).

The attachment and release of *E. coli* K12 were tested on the pCBMA-1 C2 surfaces before and after hydrolysis. Cationic pC8NMA and zwitterionic pCBMA-2 were used as the negative and the positive nonfouling control surfaces, respectively, and as the positive and the negative antimicrobial control surfaces, respectively. FIGS. 10A-10F show that large amounts of bacteria were attached to the cationic pCBMA-1 C2 and pC8NMA surfaces before hydrolysis, whereas very few bacterial cells were attached to the zwitterionic pCBMA-2 surface. In contrast to pC8NMA, pCBMA-1 C2 released the majority of cells after hydrolysis while pCBMA-2 remained nonfouling. FIG. 11 shows quantitative data for the amount of bacterial cells remaining on all three polymer surfaces before and after hydrolysis. There were similar amounts of bacterial residues on both cationic pCBMA-1 C2 and pC8NMA surfaces before hydrolysis, while the amount of attached cells on the pCBMA-2 surface is less than 0.3% of that on both cationic pCBMA-1 C2 and pC8NMA surfaces. To test the release of bacterial residues, the three surfaces were incubated in N-cyclohexyl-3-aminopropanesulfonic acid (CAPS) buffer (10 mM, pH 10.0) at 37° C. for 8 days. The pCBMA-1 C2 surfaces were hydrolyzed to poly(N-(carboxymethyl)-N,N-dimethyl-2-[(2-methyl-1-oxo-2-propen-1-yl)-oxy]ethanaminium) (pCBMA-1) and 98% of the dead bacterial cells were released. In contrast, no release of the dead cells was observed on pC8NMA surfaces (p>0.1) while pCBMA-2 surfaces retained very low bacterial adhesion.

The release of the attached bacterial cells is dependent on the conversion of cationic pCBMA-1 C2 into zwitterionic pCBMA-1. Hydrolysis rate of betaine esters is influenced by several factors, such as the length of the spacer ($L_2$) between the quaternary amine and the carboxyl groups, the nature of the hydrolyzable group, temperature, and pH value. The majority of polymer chains of the ester group used were hydrolyzed. The hydrolysis rate of the betaine esters is also slower after bacterial cells and proteins are attached to the surface. pCBMA-1 C2, which has one methylene spacer ($L_2$), was chosen and the experimental temperature was set at 37° C. to achieve a fast hydrolysis rate and to provide a physiologically relevant temperature. The protein adsorption results (see Table 2) showed that the clean, cationic pCBMA-1 C2 surface was hydrolyzed into a nonfouling zwitterionic surface after only 24 h at 37° C. and pH 10.0, while it took 48 h to form a nonfouling surface and release bacterial residues after the attachment of bacteria from an *E. coli* K12 suspension of $10^7$ cells $mL^{-1}$. When bacterial cells were attached to the pCBMA-1 C2 surface from a suspension of $10^{10}$ cells $mL^{-1}$, the release of attached bacteria took eight days under the same hydrolysis conditions.

Figure 12A:
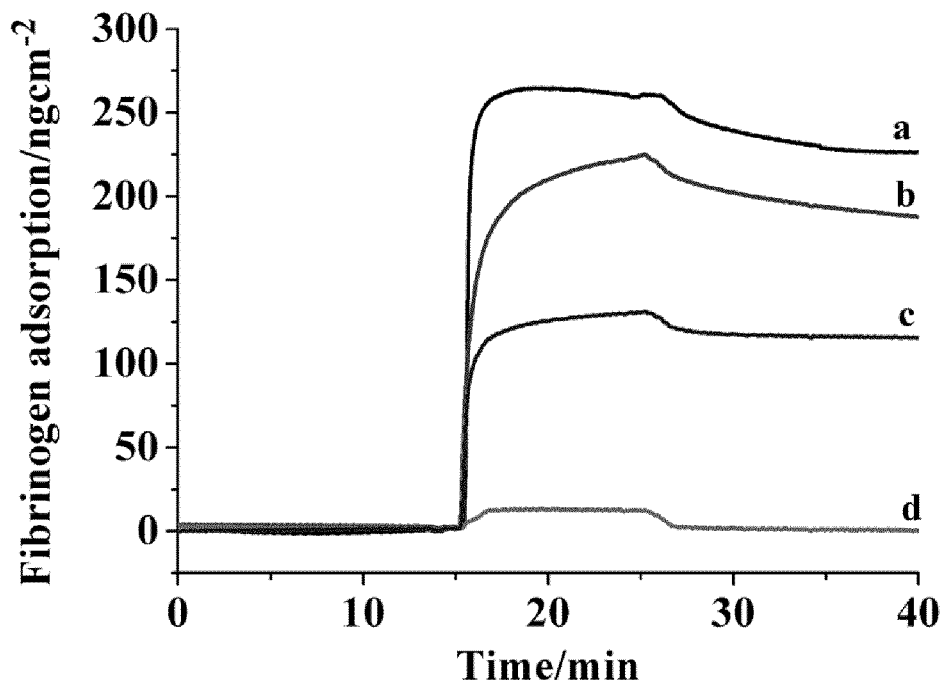
FIG. 12A compares SPR sensorgrams showing the adsorption of 1 mg mL$^{-1}$ fibrinogen in PBS buffer on the surfaces grafted with pCBMA-1 C2 via ATRP (a) before hydrolysis, and (b), (c) and (d) after 24 hr hydrolysis with water, 10 mM CEHS at pH 9.0, and 10 mM CAPS at pH 10.0, respectively.
Figure 12B:
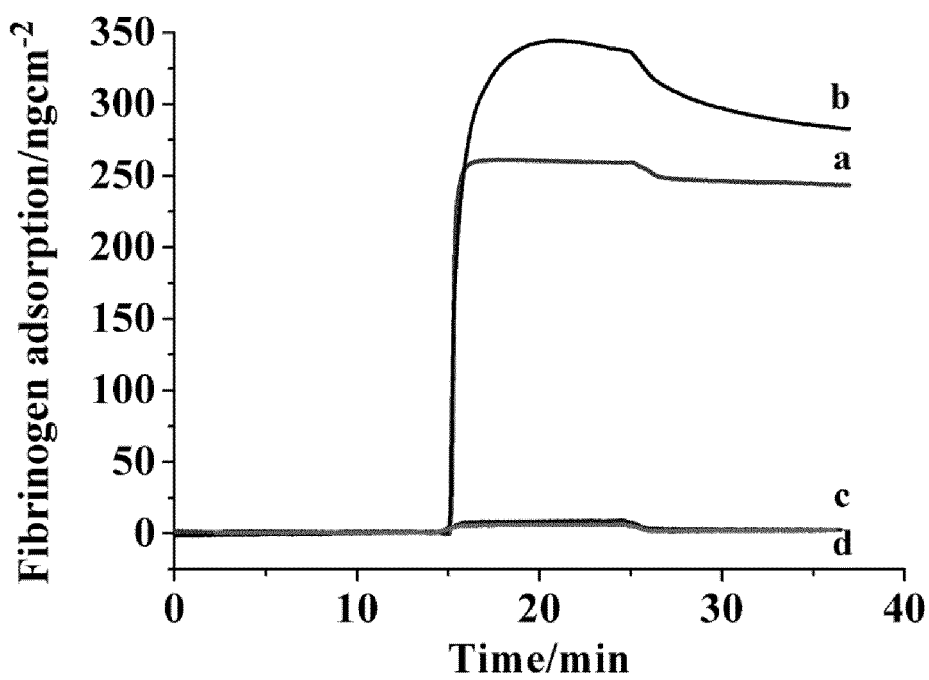
FIG. 12B compares SPR sensorgrams showing the adsorption of 1 mgmL$^{-1}$ fibrinogen in PBS buffer on the surfaces grafted with pC8NMA (a) before and (b) after 24 hr incubation with 10 mM CAPS at pH 10.0, and on the surfaces grafted with pCBMA-2 (c) before hydrolysis and (d) after 24 h of hydrolysis with 10 mM CAPS at pH 10.0.

Nonspecific protein adsorption on various surfaces was measured by a surface plasmon resonance (SPR) sensor to determine the nonfouling characteristics of the surfaces (see Table 2). Hydrolysis conditions for pCBMA-1 C2 and control surfaces were investigated in situ in the SPR sensor. FIGS. 12A and 12B show representative SPR sensorgrams for fibrinogen adsorption on pCBMA-1 C2 and control surfaces over time. The fibrinogen adsorption on pCBMA-1 C2 before hydrolysis was 229.2 ng $cm^{-2}$. After 24 h of incubation with CAPS buffer (pH 10.0), there was no measurable protein adsorption on the pCBMA-1 C2 surface, which indicated that pCBMA-1 C2 was completely hydrolyzed to nonfouling zwitterionic pCBMA-1. In contrast, hydrolysis of pCBMA-1 C2 was not complete after 24 h incubation in either water or N-cyclohexyl-2-aminoethanesulfonic acid (CEHS) buffer (pH 9.0). As shown in FIG. 12B, high fibrinogen adsorption was observed on the pC8NMA surface before and after the surface was incubated with CAPS buffer (pH 10.0) for 24 h at 37° C. However, under identical conditions, the pCBMA-2 surface still exhibited excellent nonfouling properties, with less than 2 ng $cm^{-2}$ fibrinogen absorption. This result indicates that the obtained zwitterionic surfaces are highly resistant to protein adsorption and are qualified as ultralow fouling surfaces, which are required for the surface coatings of implantable medical devices.

In this embodiment, the invention provides a switchable polymer surface that integrates antimicrobial and nonfouling properties and is biocompatible. The representative cationic polymer (i.e., precursor of pCBMA) is able to kill bacterial cells effectively and switches to a zwitterionic nonfouling surface and releases dead bacterial cells upon hydrolysis. Moreover, the resulting nonfouling zwitterionic surface can further prevent the attachment of proteins and microorganisms and reduce the formation of a biofilm on the surface. The switchable process from antimicrobial to nonfouling surfaces can be tuned through adjusting the hydrolysis rate of these polymers for specific requirements of applications.

Figure 13:
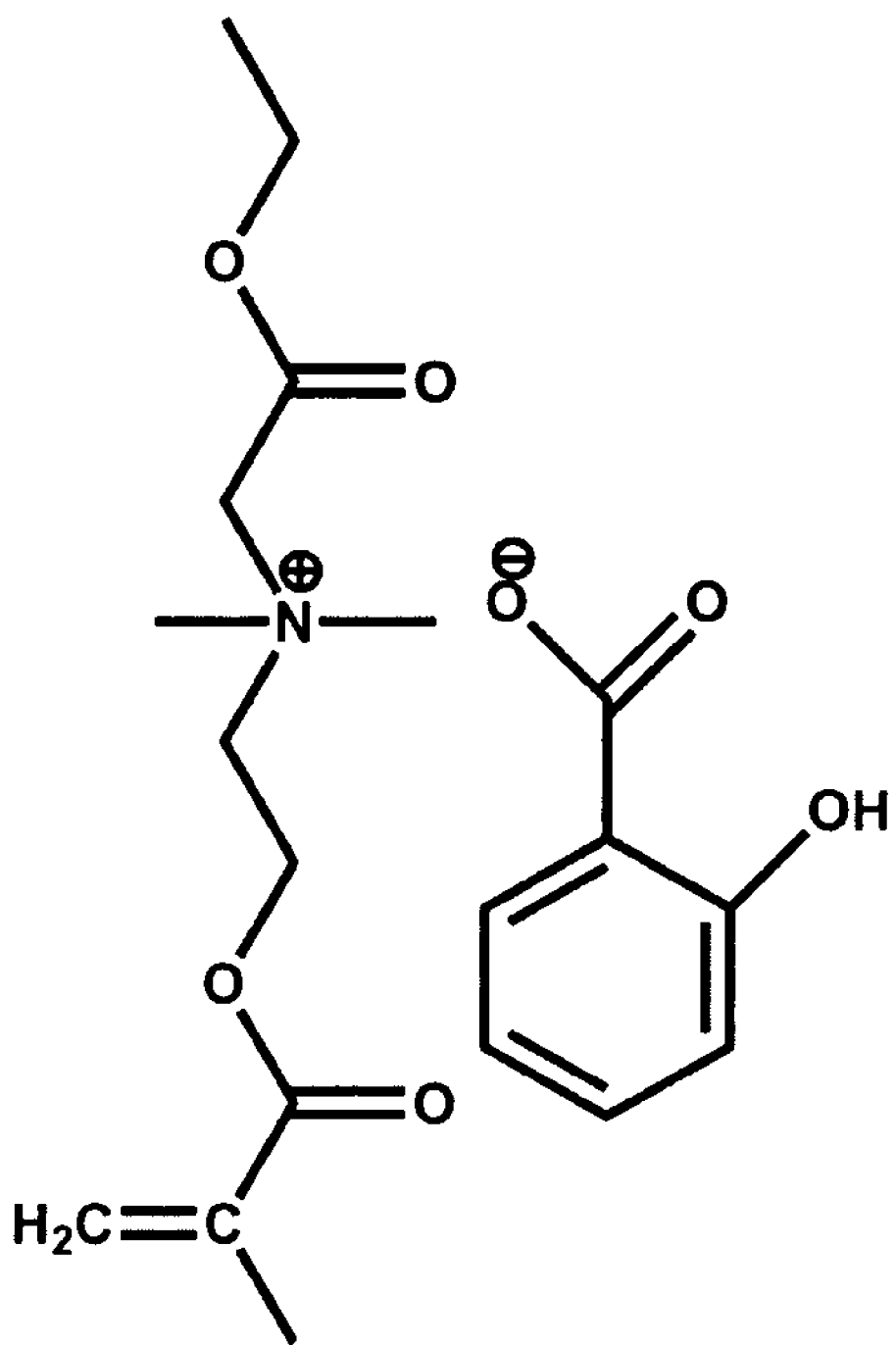
FIG. 13 illustrates the structure of a representative cationic monomers useful for making cationic polymers of the invention: CBMA-1 C2 SA, the ethyl ester of CBMA-1 having a salicylate counter ion.
Figure 14:
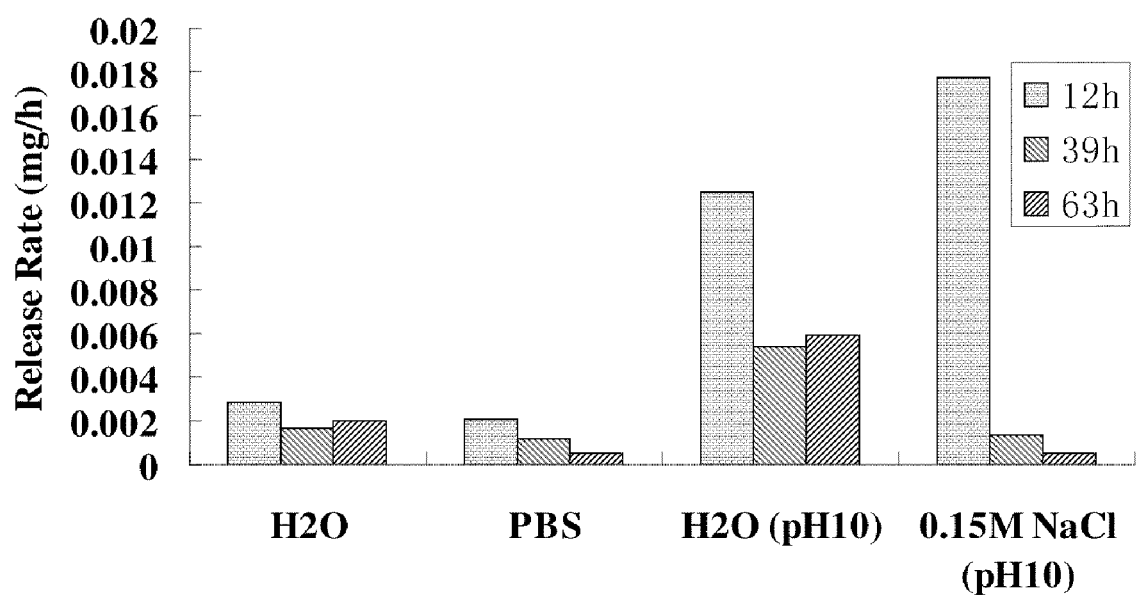
FIG. 14 compares the release rate (mg/h) of salicylic acid over time (12 h, 39 h, and 63 h) at 25° C. under four conditions from hydrogels prepared by polymerizing CBMA-1 C2 SA: (a) water, neutral pH; (b) phosphate buffered saline (PBS); (c) water, pH 10; and (d) 0.15 M aqueous sodium chloride, pH 10.
Figure 15:
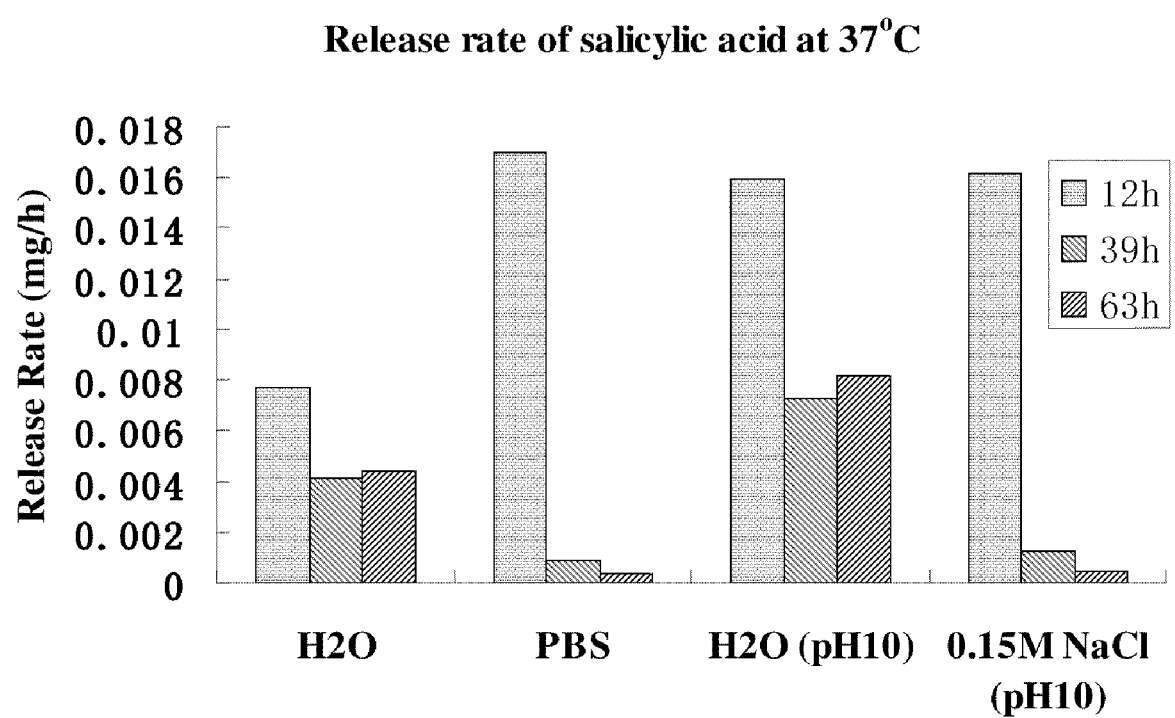
FIG. 15 compares the release rate (mg/h) of salicylic acid over time (12 h, 39 h, and 63 h) at 37° C. under four conditions from hydrogels prepared by polymerizing CBMA-1 C2 SA: (a) water, neutral pH; (b) phosphate buffered saline (PBS); (c) water, pH 10; and (d) 0.15 M aqueous sodium chloride, pH 10.

As noted above, the cationic polymers of the invention can include a hydrophobic counter ion or a counter ion having therapeutic activity (e.g., antimicrobial or antibacterial activity. A representative polymer having a salicylate counter ion (polyCBMA-1 C2) can be prepared from the monomer illustrated in FIG. 13: CBMA-1 C2 ("1" indicates one carbon between two charged groups and "C2" indicates C2 ester). PolyCBMA-1 C2 hydrogel loaded with salicylic acid (SA) as its counter ion was prepared by copolymerizing 1 mM CBMA-1 C2 SA monomer (FIG. 13) with 0.05 mM tetraethylenglycoldimethacrylate in 1 ml of solvent (ethylene glycol:water:ethanol=1:2:1) at 65° C. for 2 hours. The resulting hydrogel was soaked in DI water for 12 hours. The hydrogel was cut into round disks with 1 cm diameter. The hydrogel disks were then transferred into solutions with different pH and ionic strength and incubated at 25° C. or 37° C. At different time points the aqueous phase was completely removed and new solutions were added. The release of SA into the aqueous phase was measured by high performance liquid chromatography (HPLC). The release rate of SA is defined as the amount of released SA divided by time (mg/h). The release rate of SA from pCBMA-1 C2 SA hydrogel depends on temperature, ionic strength, and pH. FIG. 14 and FIG. 15 indicated that higher pH promotes the release of SA and that increased ionic strength can slightly increase the release rate of SA. By comparing FIG. 14 and FIG. 15, it can be observed that the elevated temperature results in a faster release of SA in water and phosphate buffered saline (PBS). The release rate of SA decreases as a function of time for all the conditions.

Therapeutic Drug Delivery

In another aspect of the invention, therapeutic agent delivery systems are provided. The cationic polymers of the invention advantageous act as carriers in the delivery of therapeutic agents that can be reversibly associated with the polymers. In one embodiment, the therapeutic agent delivery system includes a polymer of the invention and a therapeutic agent that is reversibly associative with the polymer. As used herein, the term "reversibly associative" refers to a therapeutic agent that can be effectively condensed (i.e., packaged or bound) through an associative interaction (e.g., ionic) with the cationic polymer and then released once the delivery system reaches its target. Suitable therapeutic agents include small molecules, nucleic acids (e.g., genes), proteins, and peptides having charge properties sufficient to be associated to the cationic polymers during transport to the target where the therapeutic agent dissociates from the polymer as a result of hydrolysis of the cationic polymer and its conversion to the corresponding zwitterionic polymer at the target of interest. In one embodiment, the therapeutic agent is a nucleic acid such as a DNA, RNA, or siRNA.

In certain embodiments, the polymer is a copolymer. Representative copolymers have first repeating units and second repeating units. Suitable first repeating units include tertiary (3°) amine groups and suitable second repeating units include primary (1°), secondary (2°), or quaternary (4°) amine groups. These copolymers can be designated 3°/1°, 3°/2°, and 3°/4°. In one embodiment, the second repeating units include quaternary amine groups (e.g., 3°/4° copolymer). In one embodiment, the copolymers are random copolymers. In another embodiment, the copolymers are block copolymers.

In a further aspect, the invention provides methods for administering a therapeutic agent using a cationic polymer of the invention. In the method, a therapeutic agent is administered to a subject in need thereof by administering the therapeutic agent delivery system. In one embodiment, the method includes administering an effective amount of the therapeutic agent delivery system. As used herein, the term "effective amount" refers to an amount of the delivery system that includes an amount of the therapeutic agent sufficient to affect the desired therapeutic action. Those skilled in the art can readily determine the effective amount of a therapeutic agent based on the subject, condition to be treated, and method of administration.

The preparation and usefulness of representative cationic polymers of the invention in nucleic acid delivery is described in Example 5.

Figure 16:
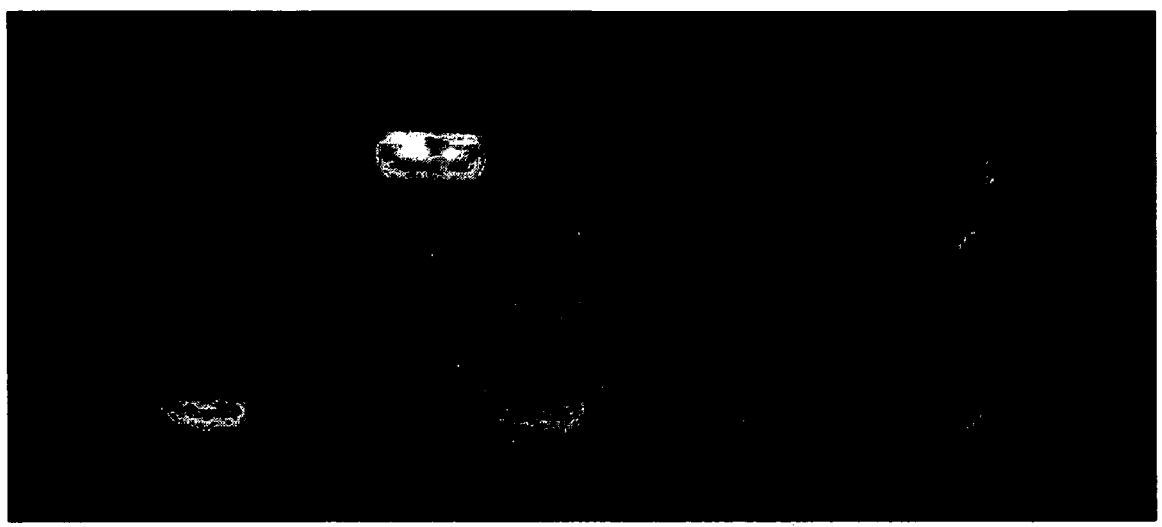
FIG. 16 is a photograph of an agarose electrophoresis gel illustrating electrophoresis retardation of DNA complexes with representative cationic polymers of the invention: lane 1, DNA only; lane 2, polyCBAA-1-ester/DNA; lane 3, hydrolyzed polyCBAA-1-ester/DNA; lane 4, polyCBAA-3-ester/DNA; lane 5, hydrolyzed polyCBAA-3-ester/DNA; lane 6, polyCBAA-5-ester/DNA; and lane 7, hydrolyzed polyCBAA-5-ester/DNA.

Representative cationic polymers, polyCBAA-1-ester (14 kDa), polyCBAA-3-ester (13 kDa), and polyCBAA-5-ester (9.6 kDa), were dissolved to provide polymer solutions and mixed with plasmid DNA. FIG. 16 shows the migration of the plasmid DNAs on an agarose gel, which can separate polymers or complexes based on their charge and size through agarose gel electrophoresis retardation. Band 1 includes DNA only. With the addition of the polymer solutions, only one band with high molecular weight was found for each case indicating that all three cationic polymers condense plasmid DNAs and form DNA/polymer complexes (bands 2, 4, and 6). PolyCBAA-1-ester/DNA complexes exhibited a strong dye signal. The agarose gel electrophoresis retardation shows the evident change before and after hydrolysis. After hydrolysis using 100 mM sodium hydroxide for 1 hour, the three polymer solutions were unable to complex plasmid DNA and all DNA in the mixtures were migrated on the agarose gel (see bands 3, 5, and 7).

Based on results from light scattering, each of the three polymers, polyCBAA-1-ester, polyCBAA-3-ester, and polyCBAA-5-ester formed complexes with an average diameter of 106, 136, and 112 nm, respectively. The particles are well formed with low polydispersity (Table 2). To allow internalization by cells, smaller sizes of polymer/DNA complexes (less than 150 nm) are desired. Results show that all three polymers can condense DNA with appropriate sizes for gene deliver carriers. All three polymer/DNA complexes bear positive charges that allow for ready dispersion in solution. The polyCBAA-1-ester, polyCBAA-2-ester, and polyCBAA-3-ester had average $\zeta$-potentials of +3.13±0.98, +6.47±0.33, and +11.80±1.44, respectively.

TABLE 2

Average effective diameters, polydispersities, and average $\zeta$-potentials of DNA/polymer complexes formed from a plasmid DNA and three polycarboxybetaine esters.

| | CB-1-ester | CB-3-ester | CB-5-ester |
|---|---|---|---|
| Average Effective Diameter (nm) | 106 ± 1 | 136 ± 2 | 113 ± 2 |
| Polydispersity | 0.13 ± 0.01 | 0.12 ± 0.39 | 0.11 ± 0.06 |
| Average Zeta Potential (mV) | +3.13 ± 0.98 | +6.47 ± 0.33 | +11.80 ± 1.44 |

Similar to other cationic polymers, the cationic polymer of the invention interact with negatively charged DNAs. The results show that the cationic polymers of the invention not only form polymer/DNA complexes, but also release DNAs after hydrolysis. Furthermore, the products of hydrolysis, zwitterionic polymers (e.g., polycarboxybetaines), are non-toxic, biocompatible, and nonfouling. For gene delivery, the polymers with the carboxybetaine ester groups can be hydrolyzed through esterases. Polycarboxybetaine esters with different spacer groups ($L_1$ and/or $L_2$), alcohol components of esters groups such as benzyl ester, can be prepared for the controllable hydrolysis intracellularly.

Furthermore, tertiary amines can be introduced as "proton sponge." Tertiary amines have pKa values around the physiological range. This property is advantageous for intracellular delivery because these amines can buffer endosomal compartments where the influx of protons causes acidification and potential DNA degradation. Amine-mediated binding of protons results in the formation of an osmotic gradient between the endosome and cytosol that can lead to vesicle swelling and rupture, known as the proton sponge effect.

Figure 17:
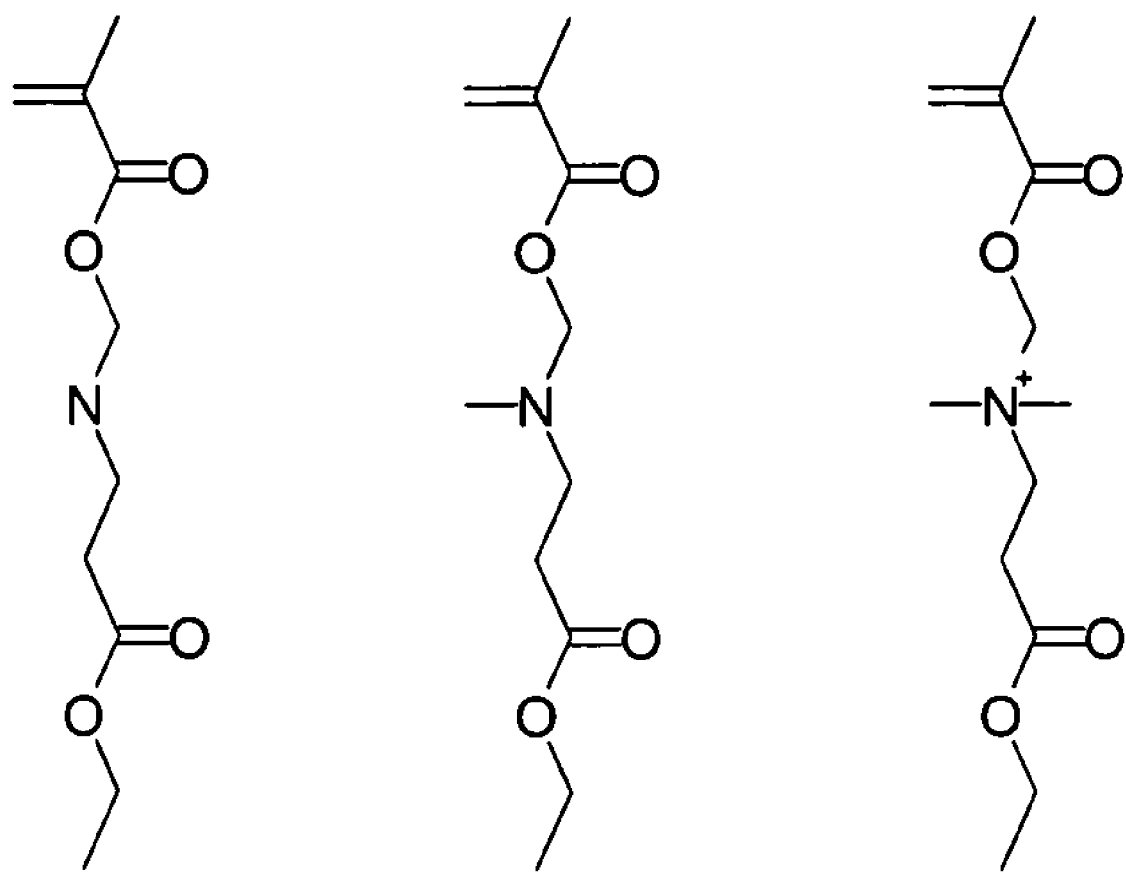
FIG. 17 illustrates the structures of secondary (2°) and tertiary (3°) analogs of quaternary (4°) carboxybetaine methacrylate ethyl ester monomers. The monomers were copolymerized at discrete ratios to provide polymers that were used to package DNA and transfect COS-7 cells at N/P=40.

In order to combine endosomal buffering capacity with biocompatibility, secondary (2°-), tertiary (3°-) and quaternary (4°-) amine analogs of carboxybetaine methacrylate (CBMA) monomers were synthesized. See FIG. 17. The monomers were copolymerized at ratios of 100%/0%, 75%/25%, 50%/50%, 25%/75%, and 0%/100%, resulting in 30-35 kDa polymers.

Figure 18:
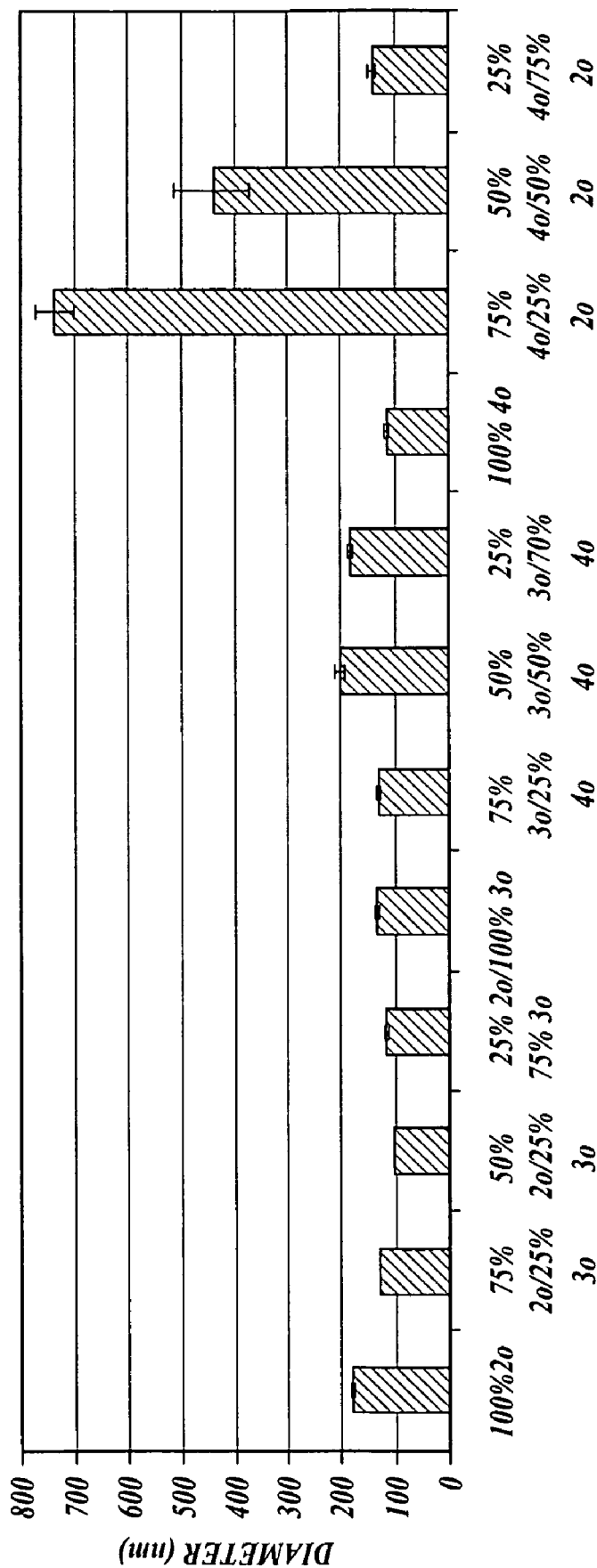
FIG. 18 is a graph of nanoparticle size for the homopolymers and copolymers prepared from the monomers illustrated in FIG. 17: 100% 2°, 100% 3°, 100% 4°, 75% 2°/25% 3°, 75% 3°/25% 4°, 75% 4°/25% 2°, 50% 2°/50% 3°, 50% 3°/50% 4°, 50% 4°/50% 2°, 25% 2°/75% 3°, 25% 3°/75% 4°, 25% 4°/75% 2°. It was found that the all polymers condensed DNA into nanoparticles small enough to enter the cells via clathrin-mediated endocytosis with the exception of 75% 4°/25% 2° and 50% 4°/50% 2° copolymers.
Figure 19:
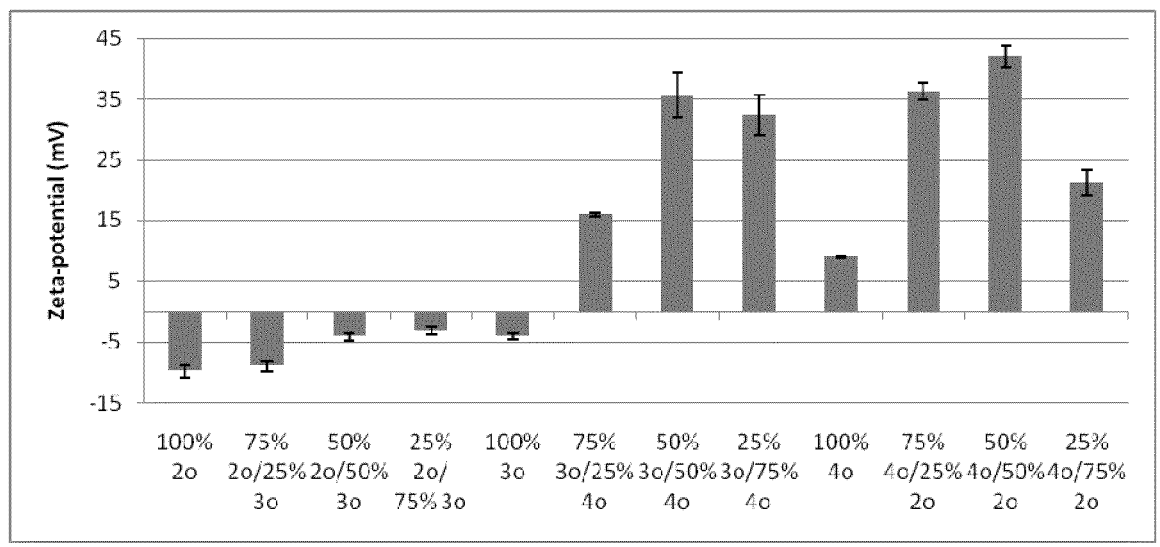
FIG. 19 is a graph of nanoparticle surface charge for the homopolymers and copolymers prepared from the monomers illustrated in FIG. 17: 100% 2°, 100% 3°, 100% 4°, 75% 2°/25% 3°, 75% 3°/25% 4°, 75% 4°/25% 2°, 50% 2°/50% 3°, 50% 3°/50% 4°, 50% 4°/50% 2°, 25% 2°/75% 3°, 25% 3°/75% 4°, 25% 4°/75% 2°. All 2°/4° and 3°/4° were positively charged, while all 2°/3° were negatively charged.

The polymers were then used to condense DNA encoding the luciferase gene into discrete nanoparticles. The size and surface charge of the nanoparticles was measured on a Brookhaven ZetaPALS instrument (see FIGS. 18 and 19, respectively). It was found that the all polymers condensed DNA into nanoparticles small enough to enter the cells via clathrin-mediated endocytosis with the exception of 75% 4°/25% 2° and 50% 4°/50% 2° copolymers. All 3°/4° and 4°/2° copolymers condensed DNA into positively charged nanoparticles, while all 2°/3° copolymer nanoparticles were negatively charged. The positive charge will allow electrostatic interaction with the cells in the absence of specific binding.

The nanoparticles were then used to transfect COS-7 cells with the luciferase gene. Only cells transfected with nanoparticles from 3°/4° mixed polymers, 100% 40, and 75% 4°/25% 2° had measurable expression of the delivered gene. The 50/50 3°/4° copolymer was an order-of-magnitude more efficient at transfection than the other copolymers.

Figure 20:
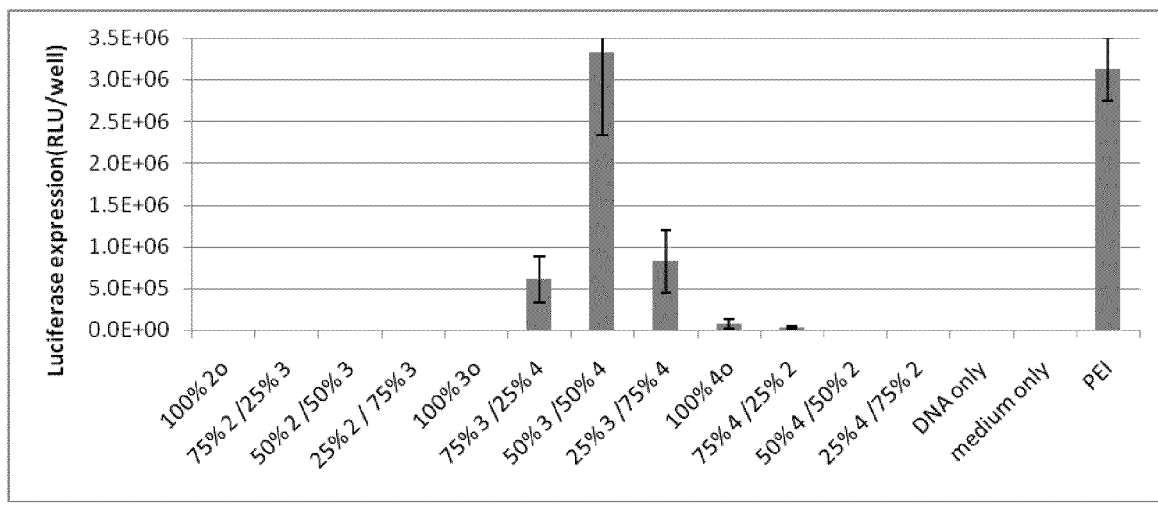
FIG. 20 is a graph comparing transfection efficiency (COS-7 cells) of poly(ethyleneimine) (PEI) to the homopolymers and copolymers prepared from the monomers illustrated in FIG. 17: 100% 2°, 100% 3°, 100% 4°, 75% 2°/25% 3°, 75% 3°/25% 4°, 75% 4°/25% 2°, 50% 2°/50% 3°, 50% 3°/50% 4°, 50% 4°/50% 2°, 25% 2°/75% 3°, 25% 3°/75% 4°, 25% 4°/75% 2°. COS-7 cells were transfected with the nanoparticles prepared via condensation of DNA by the mixed-amine polymers.

After transfection, the transfected cell colonies were tested for protein content as a measure of cell viability. It was found that all mixed-amine nanoparticles (with two exceptions) had as-good-as, if not better, cell viability than those cells treated only with medium. Transfection efficiency and cell viability of the mixed-amine nanoparticles were compared to poly(ethyleneimine) (PEI), which is widely considered as the standard for polymeric gene delivery. See FIG. 20. The 50/50 mixture of 30 and 40 CBMA esters had equivalent transfection efficiency as PEI, within error ($3.3 \times 10^6 \pm 10^6$ RLU/well for CBMA compared with $3.1 \times 10^6 \pm 4 \times 10^5$ RLU/well for PEI).

TABLE 3

Comparison of 3°/4° copolymer nanoparticles' biophysical characteristics and transfection efficiency.

| Composition | | Size (nm) | Surface Charge (mV) | Transfection efficiency |
|---|---|---|---|---|
| 3o | 4° | | | |
| 100% | — | 136 ± 1.6 | −4.2 ± 0.5 | 48.3 ± 14 |
| 75% | 25% | 132 ± 0.4 | 15.9 ± 0.3 | $6.1*10^4 \pm 2.8*10^4$ |
| 50% | 50% | 202 ± 9.4 | 40.4 ± 3.2 | $3.3*10^5 \pm 1.0*10^5$ |
| 25% | 75% | 185 ± 3.4 | 32.3 ± 3.3 | $8.2*10^4 \pm 3.8*10^4$ |
| — | 100% | 117 ± 2.2 | 8.87 ± 0.07 | $7.4*10^3 \pm 2.8*10^3$ |

Figure 21:
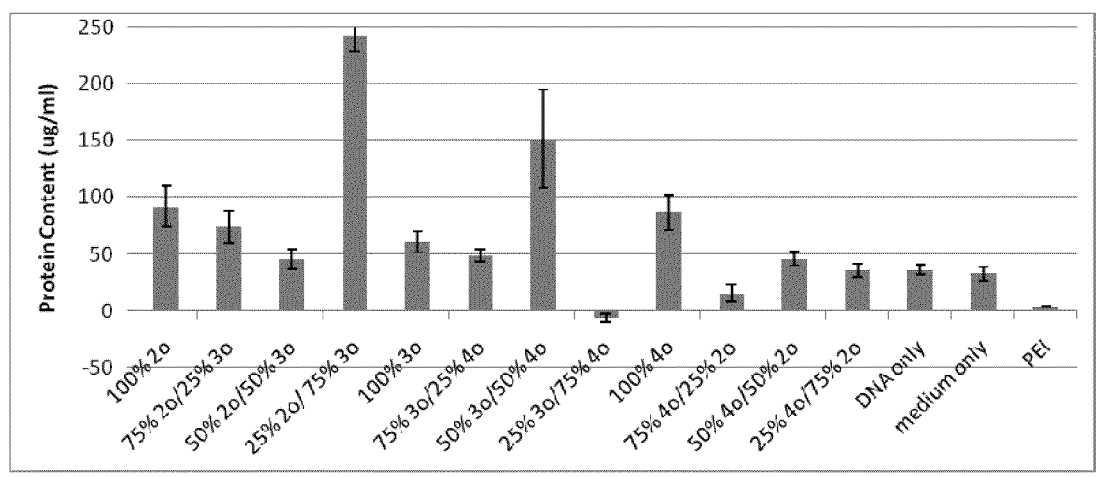
FIG. 21 is a graph comparing cell viability of cells transfected with poly(ethyleneimine) (PEI) to the homopolymers and copolymers prepared from the monomers illustrated in FIG. 17: 100% 2°, 100% 3°, 100% 4°, 75% 2°/25% 3°, 75% 3°/25% 4°, 75% 4°/25% 2°, 50% 2°/50% 3°, 50% 3°/50% 4°, 50% 4°/50% 2°, 25% 2°/75% 3°, 25% 3°/75% 4°, 25% 4°/75% 2°.

The cell viability of almost all polymers was an improvement over the cell viability of cells treated only with medium, and the 50/50 mixture of 3° and 4° CBMA esters specifically exhibited a 2-fold increase. PEI, on the other hand, had only 12% cell viability in our system. See FIG. 21. The 50/50 mixture of 3° and 4° CBMA ester copolymer has the same transfection ability as PEI and provides a 25-fold increase in cell viability.

Figure 22:
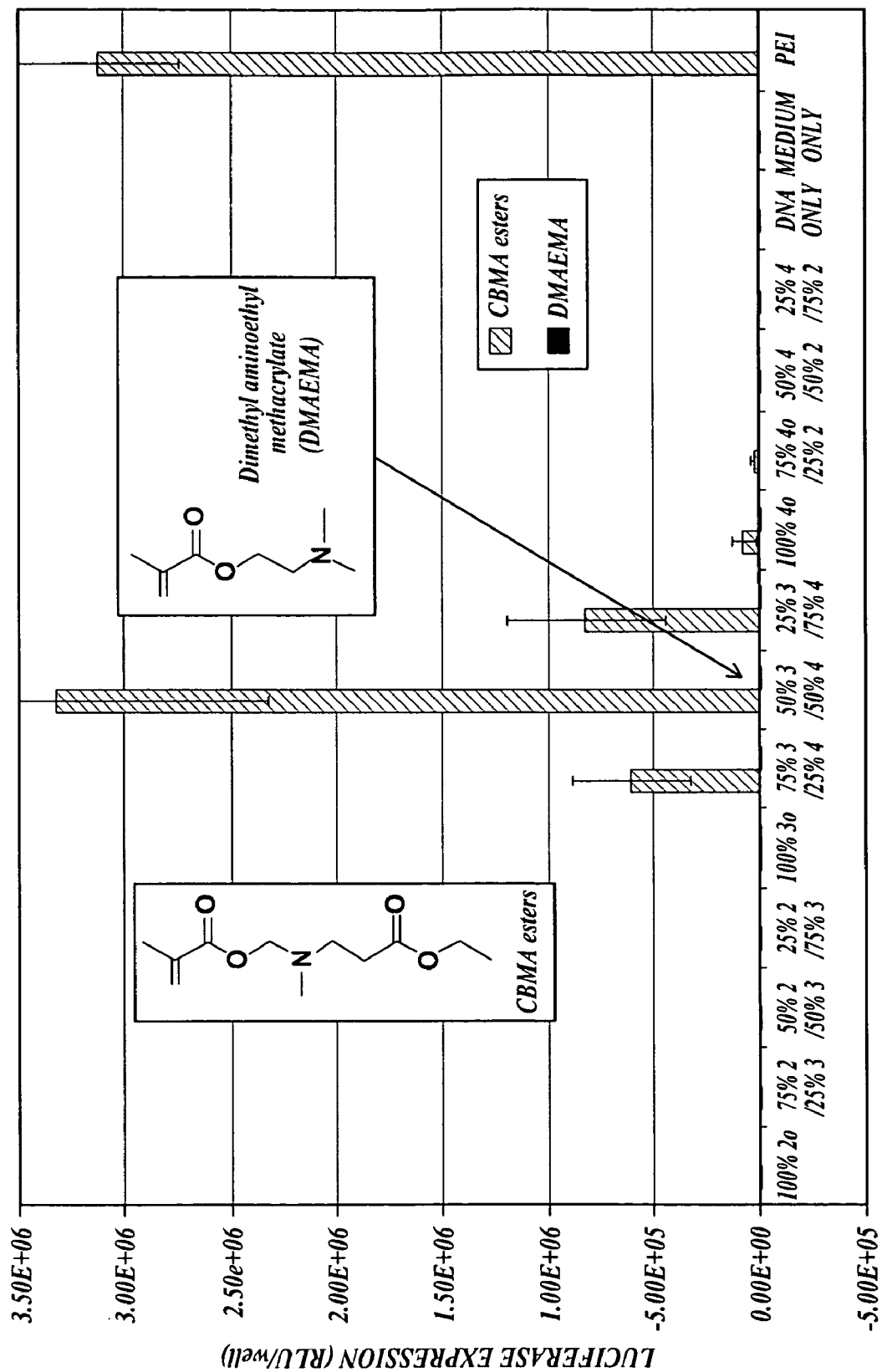
FIG. 22 is a graph comparing transfection with hydrolyzable tertiary amine CBMA ester or non-hydrolyzable tertiary amine dimethyl aminoethyl methacrylate.

To test the importance of the hydrolytic moiety on the monomers, the tertiary monomer was replaced with dimethyl aminoethyl methacrylate (DMAEMA). DMAEMA is structurally very similar to the 3° analogue of CBMA ethyl ester, but its side chain is truncated after the amine group. Thus, it would be expected to have the same endosomal buffering capacity, but lack the ability to hydrolyze to become zwitterionic. When DMAEMA monomer was copolymerized with the same 2° and 4° monomers, the resulting copolymers exhibited only baseline transfection, indicating that the hydrolysis of the ethyl ester group is the key to the transfection ability of the 3° CBMA esters. See FIG. 22.

The success of the copolymer prepared from the 50/50 mixture of 3° and 4° CBMA esters can be attributed to its balance of positive charges, which allow it to package the DNA into discretely sized and positively charged nanoparticles, and tertiary amines, which allow endosomal buffering. These characteristics are further enhanced by the ability of the polymer side-chains to hydrolyze to release DNA and leave a non-fouling and biocompatible side-product.

The following examples are provided for the purpose of illustrating, not limiting, the claimed invention.

EXAMPLES

Example 1

The Synthesis and Characterization of Representative Cationic Polymers

Materials. N-(3-dimethylaminopropyl)acrylamide (>98%) was purchased from TCI America, Portland, Oreg. Methyl bromoacetate (97%), ethyl 4-bromobutyrate (≧97.0%), ethyl 6-bromohexanoate (99%), copper (I) bromide (99.999%), bromoisobutyryl bromide (BIBB 98%), 11-mercapto-1-undecanol (97%), and 2,2'-bipyridine(BPY 99%), and 2,2'-azobis(2-methylpropionitrile) (AIBN 98%) were purchased from Sigma-Aldrich. Fibrinogen (fraction I from bovine plasma) and phosphate buffer saline (PBS, pH7.4, 0.15 M, 138 mM NaCl, 2.7 mM KCl) were purchased from Sigma Chemical Co. Ethanol (absolute 200 proof) was purchased from AAPER Alcohol and Chemical Co. Water used in experiments was purified using a Millipore water purification system with a minimum resistivity of 18.0 MΩ·cm.

ω-Mercaptoundecyl bromoisobutyrate (1) was synthesized through reaction of BIBB and 2 using a method described in Ilker, M. F.; Nuesslein, K.; Tew, G. N.; Coughlin, E. B., "Tuning the Hemolytic and Antibacterial Activities of Amphiphilic Polynorbornene Derivatives," *Journal of the American Chemical Society* 126(48):15870-15875, 2004. 1H NMR (300 MHz, CDCl$_3$): 4.15 (t, J=6.9, 2H, OCH$_2$), 2.51 (q, J=7.5, 2H, SCH$_2$), 1.92 (s, 6H, CH$_3$), 1.57-1.72 (m, 4H, CH$_2$), and 1.24-1.40 (m, 16H, CH$_2$).

Cationic Monomer Syntheses

CBAA-1-ester: (2-carboxymethyl)-3-acrylamidopropyldimethylammonium bromide, methyl ester.

N-(3-dimethylaminopropyl)acrylamide (25 mmol), methyl bromoacetate (37.5 mmol), and acetonitrile (25 mL) were added into a 100-mL round-bottom flask. The mixture was stirred under a nitrogen atmosphere for 6 hr at room temperature. The precipitate was collected, washed with ca 500 mL of anhydrous acetone. The solvent was removed on a rotary evaporator to get a white powder (96% yield). $^1$H NMR (300 MHz, D$_2$O): 2.02 (m, 2H, —CH$_2$—), 3.25 (s, 6H, N$^+$(CH$_3$)$_2$), 3.37 (t, 2H, CH$_2$—N$^+$), 3.58 (m, 2H, CH$_2$—N), 3.79 (s, 3H, O—CH$_3$), 4.29 (s, 2H, CH$_2$—C=O), 5.77 (m, 1H, CH=C—CON-trans); 6.19 (m, 1H, CH=C—CON-cis), 6.23 (m, 1H, =CH—CON—).

CBAA-3-ester: (4-carboxypropyl)-3-acrylamidopropyldimethylammonium bromide, ethyl ester.

N-(3-dimethylaminopropyl)acrylamide (50 mmol), ethyl 4-bromobutyrate (60 mmol), and acetonitrile (25 mL) were added into a 100-mL round-bottom flask. The mixture was stirred under a nitrogen atmosphere for three days at room temperature. The solvent was removed on a rotary evaporator to get a colorless oil (92% yield). $^1$H NMR (300 MHz, D$_2$O): 1.22 (t, 3H CH$_3$), 2.00 (m, 4H, C—CH$_2$—C), 2.47 (t, 2H, CH$_2$—C=O), 3.06 (s, 6H, N$^+$(CH$_3$)$_2$), 3.28-3.35 (6H, CH$_2$—N and CH$_2$—N$^+$—CH$_2$), 4.14 (q, 2H, O—CH$_2$), 5.75 (m, 1H, CH=C—CON-trans); 6.19 (m, 1H, CH=C—CON— cis), 6.26 (m, 1H, =CH—CON—).

CBAA-5-ester: (6-carboxypentyl)-3-acrylamidopropyldimethylammonium bromide, ethyl ester.

N-(3-dimethylaminopropyl)acrylamide (50 mmol), ethyl 6-bromohexanoate (55 mmol), and acetonitrile (25 mL) were added into a 100-mL round-bottom flask. The mixture was stirred under a nitrogen atmosphere for five days at 45° C. The solvent was removed on a rotary evaporator to get a slightly yellowish oil (87% yield). $^1$H NMR (300 MHz, D$_2$O): 1.20 (t, 3H CH$_3$), 1.34 (m, 2H, C—C—CH$_2$—C—C), 1.60-1.72 (4H, C—CH$_2$—C—CH$_2$—C), 2.00 (m, 2H, N—C—CH$_2$—C—N), 2.34 (t, 2H, CH$_2$—C=O), 3.04 (s, 6H, N$^+$(CH$_3$)$_2$), 3.24-3.37 (6H, CH$_2$—N and CH$_2$—N$^+$—CH$_2$), 4.12 (q, 2H, O—CH$_2$), 5.75 (m, 1H, CH=C—CON-trans); 6.20 (m, 1H, CH=C—CON— cis), 6.24 (m, 1H, =CH—CON—).

Representative Cationic Polymer Syntheses

Surface-Initiated ATRP. Three monomers, CBAA-1-ester, CBAA-3-ester, and CBAA-5-ester, were grafted onto gold-coated SPR sensor chips or gold-coated silicon chips using surface-initiated ATRP. The preparation and characterization of the polymer brushes is described in Zhang, Z.; Chen, S.; Chang, Y.; Jiang, S., "Surface Grafted Sulfobetaine Polymers Via Atom Transfer Radical Polymerization as Superlow Fouling Coatings," *Journal of Physical Chemistry B* 110 (22): 10799-10804, 2006, and Zhang, Z.; Chen, S.; Jiang, S., "Dual-Functional Biomimetic Materials: Nonfouling Poly (carboxybetaine) with Active Functional Groups for Protein Immobilization,"*Biomacromolecules* 7(12):3311-3315, 2006, previous publications. Briefly, CuBr (1 mmol) and a SPR chip or a gold disk with a Br-thiol SAM was placed in a nitrogen-purged reaction tube. Degassed solution (pure water and methanol in a 1:1 volume ratio, 10 mL) with CBAA ester (6.5 mmol), and BPY (2 mmol, in 5 mL degassed methanol) were transferred to the tube using a syringe. After reaction for more than 1 hour under nitrogen, the SPR chip or gold disk was removed and rinsed with ethanol, water and PBS solution. The samples were stored in PBS solutions before testing.

Polymer Synthesis and Characterization

CBAA-1-ester solution of ca. 0.3 M in methanol was purged with nitrogen for 30 min. The polymerization was then performed at 60° C. for ca 48 hours under nitrogen using 3 mol % AIBN as an initiator to provide polyCBAA-1-ester. Similar methods were applied for preparation of polyCBAA-3-ester or polyCBAA-5-ester using ethanol as a solvent. The polymers were washed with ethyl ether and the solvent was then removed. The structures of the polymers were confirmed by NMR. $^1$H NMR (300 MHz, $D_2O$): polyCBAA-1-ester: 1.62 (br, 2H), 2.05 (br, 3H), 3.25-3.32 (br, 8H), 3.62 (br, 2H), 3.83 (s, 3H), 4.38 (s, 2H); polyCBAA-3-ester 1.21 (t, 3H), 1.61 (br, 2H), 2.04 (br, 5H), 2.50 (t, 2H), 3.37 (br, 6H), 3.12 (s, 6H), 4.14 (q, 2H); polyCBAA-5-ester: 1.22 (t, 3H), 1.37 (m, 2H), 1.62-1.80 (br m, 6H), 2.01 (br, 3H), 2.39 (t, 2H), 3.03 (s, 6H), 3.24 (br m, 6H), 4.12 (q, 2H).

The molecular weight of linear polyCBAA was estimated using a Waters Alliance 2695 Separations Module equipped with a Waters Ultrahydrogel 1000 column and detected with a Waters 2414 Reflex Detector. The mobile phase was an aqueous solution at a flow rate of 0.5 mL/min. The instrument and column were calibrated with poly(ethylene oxide) standards from Polymer Laboratories. All measurements were performed at 35° C. The molecular weight of the polymer was calculated using Empower Pro from Waters.

Example 2

Representative Cationic Polymer Hydrolysis

The cationic polymers prepared as described in Example 1 were dissolved in NaOH solutions with different concentration (10 mM, 100 mM, and 1 M) in a concentration of 50 mg/mL. After an appropriate time interval, the polymer solutions were neutralized with dilute HCl solution and the water was removed by vacuum. 1H NMR spectroscopy ($D_2O$) was performed to measure the degradation rate by determining the amount of intact ester groups and comparing with other non-hydrolyzable pendant groups as inner standards. The results are illustrated in FIG. 3.

Example 3

Representative Cationic Polymer Protein Adsorption and Release

The cationic polymers prepared as described in Example 1 were evaluated for protein adsorption by surface plasmon resonance (SPR).

Protein adsorption was measured with a custom-built SPR sensor, which is based on wavelength interrogation. A SPR chip was attached to the base of the prism, and optical contact was established using refractive index matching fluid (Cargille). A dual-channel flow cell with two independent parallel flow channels was used to contain liquid sample during experiments. A peristaltic pump (Ismatec) was utilized to deliver liquid sample to the two channels of the flow cell. Fibrinogen solution of 1.0 mg/mL in PBS (0.15M, pH 7.4) was flowed over the surfaces at a flow rate of 0.05 mL/min. A surface-sensitive SPR detector was used to monitor protein-surface interactions in real time. Wavelength shift was used to measure the change in surface concentration (mass per unit area). The results are illustrated in FIGS. 5A-5C.

Example 4

Representative Cationic Polymer Antimicrobial Properties

The cationic polymers prepared as described in Example 1 were evaluated for their antimicrobial properties.

*E. coli* K12 were first cultured in separate pure cultures overnight at 37° C. on LB agar plates, which was then incubated with shaking at 37° C. for 24 h. Cultures on agar plates can be used for two weeks, if kept at 4° C. Several colonies were used to inoculate 25 ml of LB (20 g/L). These initial cultures were incubated at 37° C. with shaking at 100 rpm for 18 hours and were then used to inoculate a second culture of each species in 200 ml of appropriate medium. When the second suspended culture reached an optical density of 1.0 at 600 nm, bacteria were collected by centrifugation at 8,000×g for 10 min at 4° C. Cell pellets were washed three times with sterile phosphate buffered saline (PBS, pH7.4) and subsequently suspended in PBS to a final concentration of $10^8$ cells/mL.

Figure 6:
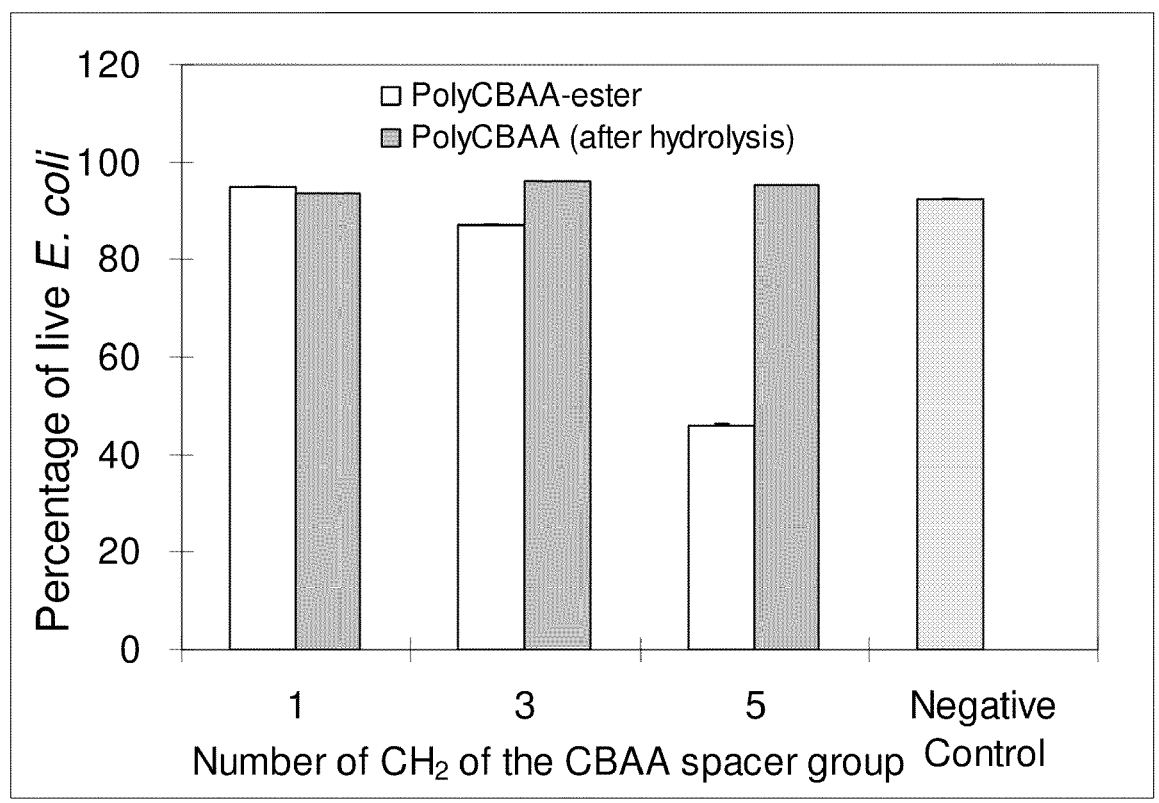
FIG. 6 is a graph comparing antimicrobial activities of three representative cationic polymers of the invention, polyCBAA-esters, before and after hydrolysis. $E.\ coli$ ($10^8$ cells/mL) was incubated with each polymer solution (repeat unit molar concentration: 2 mM) for 30 min. PBS buffer (pH 7.4 and 150 mM) is used as a negative control.

Exposure of bacterial cells to representative polymer solutions was started when the culture containing bacterial cells was added to above polymer suspension which was pre-equilibrated and shaken at 30° C., and the mixture were incubated at room temperature for 30 min. The final solution contains ca. $10^8$ cells/mL *E. coli* and 2 mM repeat unit concentration, which is the molar concentration of the repeat unit of the polymers (ca. 0.6-0.76 mg/mL based on molecular weight of CBAAs and CBAA-esters). Bacteria were stained with Live/Dead BacLight™ (Invitrogen, USA), and bacterial suspension was subsequently filtered through a polycarbonate membrane filter with 0.2 μm pore size (Millipore, USA), and observed directly with a CCD-CoolSNAP camera (Roper scientific, Inc., USA) mounted on Nikon Eclipse 80i with 100× oil lens. The number of live and dead cells was determined, respectively, through FITC and Rhodamine filters with the same microscope described in Cheng, G.; Zhang, Z.; Chen, S.; Bryers, J. D.; Jiang, S., "Inhibition of Bacterial Adhesion and Biofilm Formation on Zwitterionic Surfaces," *Biomaterials* 28(29):4192-4199, 2007. The results are illustrated in FIG. 6.

Example 5

Representative Cationic Polymer Nucleic Acid Condensation and Release

The cationic polymers prepared as described in Example 1 were evaluated for their nucleic acid condensation and release.

Preparation of Polymer/DNA Complexes and Agarose Gel Retardation Assays. The three carboxybetaine ester polymers prepared as described in Example 1 were dissolved in water with a concentration of 50 mg/mL. The polymer solutions were then diluted to a concentration of 14-19 mg/mL using DMSO. Then, water was added to make a final concentration of polymer of 1.6-2.2 mg/mL. 500 μL polymer/DMSO/water solution was added very slowly to 1.5 ml DNA solution (34.5 μg/mL) to form complexes or nanoparticles under stirring.

8.3 microliters of each nanoparticle solution was mixed with 1.7 microliters of 6× loading buffer (Novagen, Madison, Wis.), and loaded into a 0.8% agarose gel. The gel was run at 65V for 2.5 hours. The control used was 8.3 microliters 30 micrograms/mL DNA in water with 1.7 microliters 6× loading buffer. DNA bands were visualized by ethidium bromide staining. The results are illustrated in FIG. 16.

Dynamic laser light scattering and ζ potential measurements. The particle size and ζ potential measurements were made using a ZetaPALS dynamic light scattering detector (Brookhaven Instruments Corp., Holtsville, N.Y., USA; 15-mW laser, incident beam at 676 nm). Polymer/DNA complexes were prepared as described above and complexes were then diluted in 1.4 ml of 25 mM Hepes buffer, pH 7.2. Correlation functions were collected at a scattering angle of 90°, and particle sizes were calculated using the Dynamic Light Scattering Software (version 3.55). Average electrophoretic mobilities were measured using BIC PALS ζ potential analysis software (Ver 3.82).

While illustrative embodiments have been illustrated and described, it will be appreciated that various changes can be made therein without departing from the spirit and scope of the invention.

The embodiments of the invention in which an exclusive property or privilege is claimed are defined as follows:

1. A surface of a substrate, comprising a polymer covalently coupled thereto, wherein the polymer has the formula:

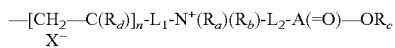

wherein
PB is a polymer backbone;
N⁺ is a cationic center;
$R_a$ and $R_b$ are independently selected from hydrogen, alkyl, and aryl;
A(=O)—$OR_c$ is a hydrolyzable group, wherein A is selected from the group consisting of C, S, SO, P, or PO, and $R_c$ is an alkyl, aryl, acyl, or silyl group that may be further substituted with one or more substituents;
$L_1$ is a linker that covalently couples the cationic center to the polymer backbone;
$L_2$ is a linker that covalently couples the cationic center to the hydrolyzable group; X— is a counter ion associated with the cationic center; and n is an integer from about 10 to about 10,000.

2. The surface of claim 1, wherein the counter ion is selected from the group consisting of C1-C20 carboxylates and C1-C20 alkylsulfonates.

3. The surface of claim 1, wherein the counter ion is a therapeutic agent.

4. The surface of claim 1, wherein the counter ion is selected from the group consisting of an antimicrobial, an antibacterial, and an antifungal agent.

5. The surface of claim 1, wherein the counter ion is selected from the group consisting of nucleic acids, amino acids, proteins, and peptides.

6. The surface of claim 1, wherein the hydrolyzable group releases a C1-C20 carboxylate on hydrolysis.

7. The surface of claim 1, wherein $R_a$ and $R_b$ are independently selected from the group consisting of hydrogen and C1-C10 straight chain and branched alkyl groups.

8. The surface of claim 1, wherein $L_1$ is selected from the group consisting of —C(=O)O—$(CH_2)_n$— and —C(=O)NH—$(CH_2)_n$—, wherein n is an integer from 1 to 20.

9. The surface of claim 1, wherein the $L_2$ is —$(CH_2)_n$—, where n is an integer from 1 to 20.

10. The surface of claim 1, wherein A is selected from the group consisting of C, SO, and PO.

11. The surface of claim 1, wherein $R_c$ is C1-C20 alkyl.

12. The surface of claim 1, wherein X- is selected from the group consisting of halide, carboxylate, alkylsulfonate, sulfate, nitrate, perchlorate, tetrafluoroborate, hexafluorophosphate, trifluoromethylsulfonate, bis(trifluoromethylsulfonyl)amide, lactate, and salicylate.

13. The surface of claim 1, wherein the polymer has a plurality of repeating units, the repeating units having the formula:

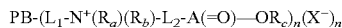

wherein
—$[CH_2$—$C(R_d)]_n$- defines a polymer backbone having n repeating units;
$R_d$ is selected from the group consisting of hydrogen, fluorine, trifluoromethyl, and C1-C6 alkyl;
n is 10 to 10,000;
N⁺ is a cationic center;
$R_a$ and $R_b$ are independently selected from hydrogen, alkyl, and aryl;
A(=O)—$OR_c$ is a hydrolyzable group, wherein A is selected from the group consisting of C, S, SO, P, or PO, and $R_c$ is an alkyl, aryl, acyl, or silyl group that may be further substituted with one or more substituents;
$L_1$ is a linker that covalently couples the cationic center to the polymer backbone;
$L_2$ is a linker that covalently couples the cationic center to the hydrolyzable group; and
X⁻ is the counter ion associated with the cationic center.

14. The surface of claim 1, wherein the polymer is a homopolymer.

15. The surface of claim 1, wherein the polymer is a copolymer.

16. The surface of claim 1, wherein the polymer is a random copolymer.

17. The surface of claim 1, wherein the polymer is a block copolymer.

18. The surface of claim 1, wherein the substrate is selected from the group consisting of a particle, a drug carrier, a non-viral gene delivery system, a biosensor, a membrane, an implantable sensor, a subcutaneous sensor, an implant, and a contact lens.

19. The surface of claim 1, wherein the substrate is a medical device.

20. The surface of claim 1, wherein the substrate is an implantable medical device selected from the group consisting of an ear drainage tube, feeding tube, glaucoma drainage tube, hydrocephalous shunt, keratoprosthesis, nerve guidance tube, urinary catheter, tissue adhesive, x-ray guide, artificial joint, artificial heart valve, artificial blood vessel, pacemaker, left ventricular assist device (LVAD), artery graft, tissue scaffold, and stent.

* * * * *

UNITED STATES PATENT AND TRADEMARK OFFICE
CERTIFICATE OF CORRECTION

| | | Page 1 of 1 |
|---|---|---|
| PATENT NO. | : 8,268,301 B2 | |
| APPLICATION NO. | : 12/274218 | |
| DATED | : September 18, 2012 | |
| INVENTOR(S) | : S. Jiang et al. | |

It is certified that error appears in the above-identified patent and that said Letters Patent is hereby corrected as shown below:

In the Specification

| COLUMN | LINE | ERROR |
|---|---|---|
| 1 | 15-19 | "This invention was made with Government support under Grant No. N000140410409 awarded by the Office of Naval Research and Grant No. AB06BAS759 awarded by the Defense Threat Reduction Agency, U.S. Department of Defense. The Government has certain rights in the invention." should read |
| | | --This invention was made with Government support under grant N00014-04-1-0409 awarded by the Office of Naval Research, grant HDTRA1-07-1-0033 awarded by the Defense Threat Reduction Agency, and grant DMR-0705907 awarded by the National Science Foundation. The Government has certain rights in the invention.-- |

Signed and Sealed this
Second Day of September, 2014

Michelle K. Lee
*Deputy Director of the United States Patent and Trademark Office*